US012754441B2

(12) United States Patent
Neal et al.
(10) Patent No.: US 12,754,441 B2
(45) Date of Patent: Oct. 6, 2026

(54) TILT AND OFFSET CORRECTION FOR SCLERAL AND NORMAL CONTACT LENSES

(71) Applicant: Wavefront Dynamics, Inc., Albuquerque, NM (US)

(72) Inventors: Daniel R. Neal, Tijeras, NM (US); Xifeng Xiao, Albuquerque, NM (US)

(73) Assignee: WaveFront Dynamics, Inc., Albuquerque, NM (US)

( * ) Notice: Subject to any disclaimer, the term of this patent is extended or adjusted under 35 U.S.C. 154(b) by 411 days.

(21) Appl. No.: 18/457,697

(22) Filed: Aug. 29, 2023

(65) Prior Publication Data

US 2024/0069361 A1 Feb. 29, 2024

Related U.S. Application Data

(60) Provisional application No. 63/402,351, filed on Aug. 30, 2022.

(51) Int. Cl.
*G02C 7/04* (2006.01)
*A61B 3/10* (2006.01)

(52) U.S. Cl.
CPC ............ *G02C 7/047* (2013.01); *A61B 3/1015* (2013.01)

(58) Field of Classification Search
CPC .............................. G02C 7/047; A61B 3/1015
USPC .......................................................... 351/247
See application file for complete search history.

(56) References Cited

U.S. PATENT DOCUMENTS 5,293,533 A * 3/1994 Klyce .................... A61B 3/107 351/212
5,686,981 A * 11/1997 Anan ..................... A61B 3/135 351/212
8,696,117 B2 * 4/2014 Svochak .................. A61B 3/14 351/247

(Continued)

OTHER PUBLICATIONS

Wang X, Dong J, Wang X, Wu Q. IOL tilt and decentration estimation from 3 dimensional reconstruction of OCT image. PLoS One. 2013;8(3):e59109. doi: 10.1371/journal.pone.0059109. Epub Mar. 15, 2013. PMID: 23554982; PMCID: PMC3598664 (Year: 2013).*

(Continued)

*Primary Examiner* — Zachary W Wilkes
(74) *Attorney, Agent, or Firm* — Quinn IP Law

(57) ABSTRACT

A method for correcting aberrations of a patient's eye with a customized contact lens, including determining an optimal XY location and an optimal angular orientation, a, for placing correction optics on the customized contact lens by using an optical instrument to measure XY offsets (ΔX, ΔY) and X, Y, Z tilt angles, ($\theta_x$, $\theta_y$, α), respectively, of a predicate contact lens while disposed on the patient's eye is disclosed. The predicate contact lens and the customized contact lens can be a scleral contact lens or a normal contact lens. The optical instrument can comprise a wavefront aberrometer and/or a corneal topographer. The correction optics include a wavefront-customized contact lens with a built-in, optimized wavefront-guided correction patch. The predicate contact lens can include three or more fiducial marks inside of the pupil, which can be used to determine the XY center of the predicate contact lens when placed on the patient's eye.

14 Claims, 18 Drawing Sheets

(56) References Cited

U.S. PATENT DOCUMENTS

| | | | | |
|---|---|---|---|---|
| 8,727,534 | B2 * | 5/2014 | Kim | A61B 3/107<br>351/212 |
| 10,901,238 | B2 * | 1/2021 | Heavyside | G02C 7/021 |
| 11,576,574 | B2 * | 2/2023 | van der Steen | A61B 90/39 |
| 11,762,219 | B2 * | 9/2023 | Legerton | A61B 3/111<br>351/159.02 |
| 12,446,772 | B2 * | 10/2025 | Xiao | G02C 7/047 |
| 2012/0188508 | A1 * | 7/2012 | Kim | A61B 3/103<br>351/247 |
| 2018/0210230 | A1 * | 7/2018 | Heavyside | G02C 7/047 |
| 2019/0274543 | A1 * | 9/2019 | van der Steen | G02B 1/043 |
| 2022/0317476 | A1 * | 10/2022 | Legerton | A61B 3/111 |

OTHER PUBLICATIONS

Ticak A, Marsack; et al. A Comparison of Three Methods to Increase Scleral Contact Lens On-Eye Stability. Eye Contact Lens. Nov. 2015; 41(6):386-90. doi: 10.1097/ICL.0000000000000145. PMID: 25943050; PMCID: PMC4630135 (Year: 2015).*

Vincent et al., "A topographical method to quantity scleral contact lens decentration," Contact Lens and Anterior Eye, 42(4) 462-466, 2019.

Fadel"The influence of limbal and scleral shape on scleral lens design," Contact Lens and Anterior Eye, 41, 321-328, 2018.

Wang at el., "Effects of decentration of wavefront-corrected intraocular lenses on the higher-order aberration of the eye," Arch. Ophthalmol., 123, 1226-1230, 2005.

Dai, Wavefront Optics: for vision correction, Chapter 8, SPIE Press, 2008.

Neal et al., "Restoration for Normal Optical Quality with Wavefront Guided Scleral Lenses," WaveFront Dynamics Inc. 2023.

Xiao et al., "Scleral contact lens tilt measurement for higher order aberrations correction," Poster Presentation, 148, Global Specialty Lens Symposium, 2023.

* cited by examiner

Fiducial Marks Outside of Pupil

TILT AND OFFSET CORRECTION FOR SCLERAL AND NORMAL CONTACT LENSES

REFERENCE TO RELATED APPLICATIONS

This application claims the priority benefit of U.S. Provisional Application Ser. No. 63/402,351 filed Aug. 30, 2022, which is incorporated by reference in its entirety.

INTRODUCTION

Keratoconus, pellucid marginal degeneration, corneal transplants, and other cornea abnormalities lead to a distorted cornea. This can restrict the visual acuity and quality of vision of the affected individuals. Currently it is estimated that about 1 in 375 people have keratoconus. Combined with the other conditions, 1-2% of the population suffers from degraded vision that is the result of a distorted cornea.

With the advent of wavefront-driven refractive surgery (e.g., LASIK and PRK), for some individuals these imperfections can be measured with a wavefront-sensing aberrometer, and the measurements are used to guide the laser's sculpting of the cornea. While this technique can be quite effective, refractive surgery is limited to those patients that have a sufficiently large corneal thickness to support the required depth of ablation. Unfortunately, it is usually because of a thin or weak cornea that the aberrations develop. So, the very people that need a wavefront-guided surgical approach the most are ineligible for LASIK or PRK.

It has recently become possible to treat these individuals with a wavefront-customized Contact Lens (CL) using the same approach. This can successfully correct for the corneal distortion, even with quite strong aberrations. For this to be effective, however, the contact lens must be very stable on the eye so that the region on the contact lens with the wavefront-guided correction patch remains aligned with the pupil. This has led to the use of large-diameter, scleral contact lenses for this purpose, since these are generally much more stable than cornea rigid gas permeable (RGP) or soft contact lenses.

By design, a scleral contact lens rests on the sclera of the eye and not on the cornea. Most of these lenses are designed to vault over the cornea so as not to touch it in any way. Thus, the fit of the scleral lens depends not as much on the corneal shape as it does on the sclera's shape. Various technologies have been developed to profile the eye, including the sclera, to determine the scleral shape and, hence, the fit of the contact lens. These include stereophotography, Scheimflug profilometry, Optical Coherence Tomography (OCT), impression profilometry, and 3D imaging.

The sclera is not necessarily concentric with the cornea. Also, a scleral lens is generally tilted and offset with respect to the cornea. The light is collected through the pupil, so a special alignment is required between the location of the wavefront-guided correction patch on the customized contact lens and the cornea.

The tilt of a scleral contact lens is primarily determined by where it rests on the sclera, which in turn depends on the eye's scleral shape. Scleral lenses also usually have a deep sagittal height, e.g., $S_0$=5-6 mm, and so any amount of tilt can result in a significant XY offset between the optical center of the pupil and the physical center of the tilted scleral contact lens. Thus, the measured position of the wavefront-guided correction patch may not be adequately determined using the contact lens' edge, or fiducial marks located near the outer edge of the contact lens. This can result in errors in properly placing the wavefront-guided correction patch since the designed correction patch does not align properly with the actual aberrations of the eye. Thus, determining the tilt and offset of a scleral or corneal contact lens is important to achieving optimal wavefront-guided corrections.

SUMMARY

A method is disclosed for correcting aberrations of a patient's eye with a customized contact lens, including determining an optimal XY location and an optimal angular orientation, a, for placing correction optics on the customized contact lens by using an optical instrument to measure XY offsets (ΔX, ΔY) and X, Y, Z tilt angles, ($\theta_x$, $\theta_y$, α), respectively, of a predicate contact lens while disposed on the patient's eye. The predicate contact lens and the customized contact lens can be a scleral contact lens or a corneal contact lens. The optical instrument can comprise a wavefront aberrometer and/or a corneal topographer. The correction optics include a wavefront-customized contact lens with a built-in, optimized wavefront-guided correction patch. The predicate contact lens can include three or more fiducial marks inside of the pupil, which can be used to determine the geometric center of the predicate contact lens in the XY plane when placed on the patient's eye.

An alternative method (i.e., method B) can also be used that does not require the use of fiducial marks on the predicate contact lens.

A contact lens' physical center is typically different (i.e., offset in the XY plane) from the center of the pupil. Typical amounts of XY offset are less than or equal to about 1 mm. The XY offset (ΔX, ΔY) of the contact lens' physical center from the pupil's optical center is measured. Then, the center of the wavefront-guided correction patch is moved in the XY plane to match the location of the measured optical center (i.e., pupil center). This process works for both wavefront-guided customized contact lenses and for regular (non-customized) contact lenses, as the improved centering technique helps regular contact lenses (even without using wavefront-guided correction techniques). The process can also be applied to both scleral and normal contact lenses.

In an embodiment, a method for correcting one or more aberrations of a patient's eye with a customized contact lens includes determining an optimal XY location and an optimal angular orientation, a, for placing correction optics on the customized contact lens by using an optical instrument to measure XY offsets (ΔX, ΔY) and X, Y, Z tilt angles, ($\theta_x$, θy, θz), respectively, of a predicate contact lens while disposed on the patient's eye. The optical instrument can be a wavefront aberrometer, a slit lamp camera, or other instrument that can take an image of the eye. Alternatively, the optical instrument can be a corneal topographer, an anterior OCT or a Scheimflug imager.

In an example, the correction optics can include a wavefront-customized contact lens with a built-in wavefront-guided correction patch that is placed at the optimal XY location and the optimal angular orientation of the customized contact lens. Both the predicate contact lens and the wavefront-guided customized contact lens can be scleral contact lenses or corneal contact lenses (e.g., rigid contact lenses). Alternatively, the predicate lens can be a patient's habitual scleral lens.

In some embodiments, the predicate contact lens can include two or more fiducial marks arranged in a known geometric pattern. In general, the fiducial marks can be located at the edge of, or are located inside of, the patient's pupil. In one example, three fiducial marks can be geometrically arranged in a 45/45/90 right isosceles triangular pattern.

The total number of fiducial marks on a predicate CL can comprise 2, 3, 4, 5, 6, 7, 8, 9, or 10 fiducial marks, arranged in known (pre-defined) symmetrical or asymmetrical patterns about the X- and Y-axes.

In an example, where the fiducial marks are arranged in an isosceles triangle, the method can include calculating a real center, ($X_c$, $Y_c$), of the predicate contact lens by averaging X- and Y-coordinates of the three or more fiducial marks. The real CL center ($X_c$, $Y_c$) is located at the center of a 45/45/90 right isosceles triangle's hypotenuse and can be easily obtained from the average position of two corner marks.

Alternatively, the method can include calculating a real center, ($X_c$, $Y_c$), of the predicate contact lens by: (1) providing a Radius of Curvature=R, Sagittal height=$S_0$, and Diameter=d of the predicate contact lens; (2) measuring XY coordinates ($X_v$, $Y_v$) of a Corneal Vertex Normal by using Corneal Topography (CT) and/or visual Eye Imaging (EI) techniques; (3) determining a virtual center ($X_e$, $Y_e$) of the predicate CL by using the diameter, d, and by fitting an edge of the predicate contact lens to a circle or ellipse; (4) calculating X- and Y-tilt angles ($\theta_x$, $\theta_y$) and obtaining a real contact lens center ($X_c$, $Y_c$), by using equations (7) and (8), as follows:

$$\theta_x = \tan^{-1}\frac{X_v - X_e}{R} \quad \text{(Eq. 7)}$$

$$\theta_x = \tan^{-1}\frac{X_v - X_e}{R} \quad \text{(Eq. 8)}$$

and (5) calculating the physical center ($X_c$, $Y_c$) of the predicate contact lens by using equations (9) and (10), as follows:

$$X_c = X_e + S_0\sin\theta_x \text{ and} \quad \text{(Eq. 9)}$$

$$Y_c = Y_e + S_0\sin\theta_y; \quad \text{(Eq. 10)}$$

wherein no fiducial marks are placed on the predicate contact lens.

Additionally, the method can include measuring Corneal Vertex coordinates ($X_v$, $Y_v$) by using Purkinje reflections from the patient's cornea. The method can further include calculating the pair of XY offsets (ΔX, ΔY) by using equations (11, 12, 13, and 14), as follows:

$$L = \sqrt{(X_P - X_c)^2 + (Y_P - Y_c)^2} \quad \text{(Eq. 11)}$$

$$\phi = \tan^{-1}\left(\frac{Y_P - Y_c}{X_P - X_c}\right) \quad \text{(Eq. 12)}$$

$$\Delta X = L\cos(\phi - \alpha) \quad \text{(Eq. 13)}$$

$$\Delta Y = L\sin(\phi - \alpha). \quad \text{(Eq. 14)}$$

In an embodiment, the predicate contact lens' tilt is measured by determining an optical axis normal to an optical Z-axis of the optical instrument. Additionally, the optical Z-axis normal can be determined by measuring Purkinje reflections from light sources projected onto the contact lens. The optical Z-axis normal position can be corrected for misalignment of the eye when looking into the optical instrument. The optical Z-axis normal position can be found by projecting light through an objective front lens of the optical instrument. The optimum location of the correction optics can be measured by using a projected pattern of fiducial marks disposed on the predicate contact lens.

In one example, a method of correcting aberrations of a patient's eye with a customized contact lens can include: (a) placing a predicate contact lens on the patient's eye; (b) measuring a pair of XY offsets (ΔX, ΔY) of a center of the predicate contact lens, while sitting on the patient's eye; (c) measuring a rotation angle, a, of the predicate contact lens, while sitting on the patient's eye; (d) determining an optimal XY location and an optimal angular orientation of a wavefront-guided correction patch on the customized contact lens by using the measured pair of XY offsets (ΔX, ΔY) and the measured rotation angle, a, of the predicate contact lens; (e) defining a center of the wavefront-guided correction patch; and (f) adjusting a placement of the wavefront-guided correction patch on the customized contact lens by: (1) placing the center of the wavefront-guided correction patch at the optimal XY location by X- and Y-distances equal to the measured ΔX and ΔY offsets, respectively, and by (2) rotating the wavefront-guided correction patch by the rotation angle, a, to the optimal angular orientation.

In a different example, residual Higher Order Aberrations (HOAs) of a patient's eye are minimized by fabricating and using an optimized wavefront-customized contact lens, wherein the method includes: (α) measuring one or more residual HOAs of a patient's eye with an optical instrument; (b) designing a wavefront-guided correction patch for a wavefront-customized contact lens by using the measured HOAs of the patient's eye; (c) placing a predicate contact lens on the patient's eye; (d) measuring a pair of XY offsets (ΔX, ΔY) of a center ($X_c$, $Y_c$) and a rotation angle, α, of the predicate contact lens, while sitting on the patient's eye; (e) determining an optimal XY location and an optimal angular orientation of the wavefront-guided correction patch on the wavefront-customized contact lens by using the measured pair of XY offsets (ΔX, ΔY) and the measured rotation angle, α, of the predicate contact lens; (f) defining a center of the wavefront-guided correction patch; (g) adjusting a placement of the wavefront-guided correction patch on a contact lens by: (1) placing the center of the standard wavefront-guided correction patch at the optimal XY location using the measured pair of ΔX and ΔY offsets, and (2) rotating the wavefront-guided correction patch to the optimal angular orientation by using the rotation angle, α; (h) fabricating an optimized wavefront-customized contact lens by positioning the wavefront-guided correction patch at the optimal XY location and the optimal angular orientation; and (i) minimizing the HOA's of the patient's eye by using the optimized wavefront-customized contact lens on the patient's eye.

In an embodiment, a predicate scleral contact lens can include two or more fiducial marks disposed on the predicate scleral contact lens. In an alternative embodiment, the predicate lens is a traditional scleral lens that was designed with only sphere and cylinder correction.

DETAILED DESCRIPTION

Figure 1:
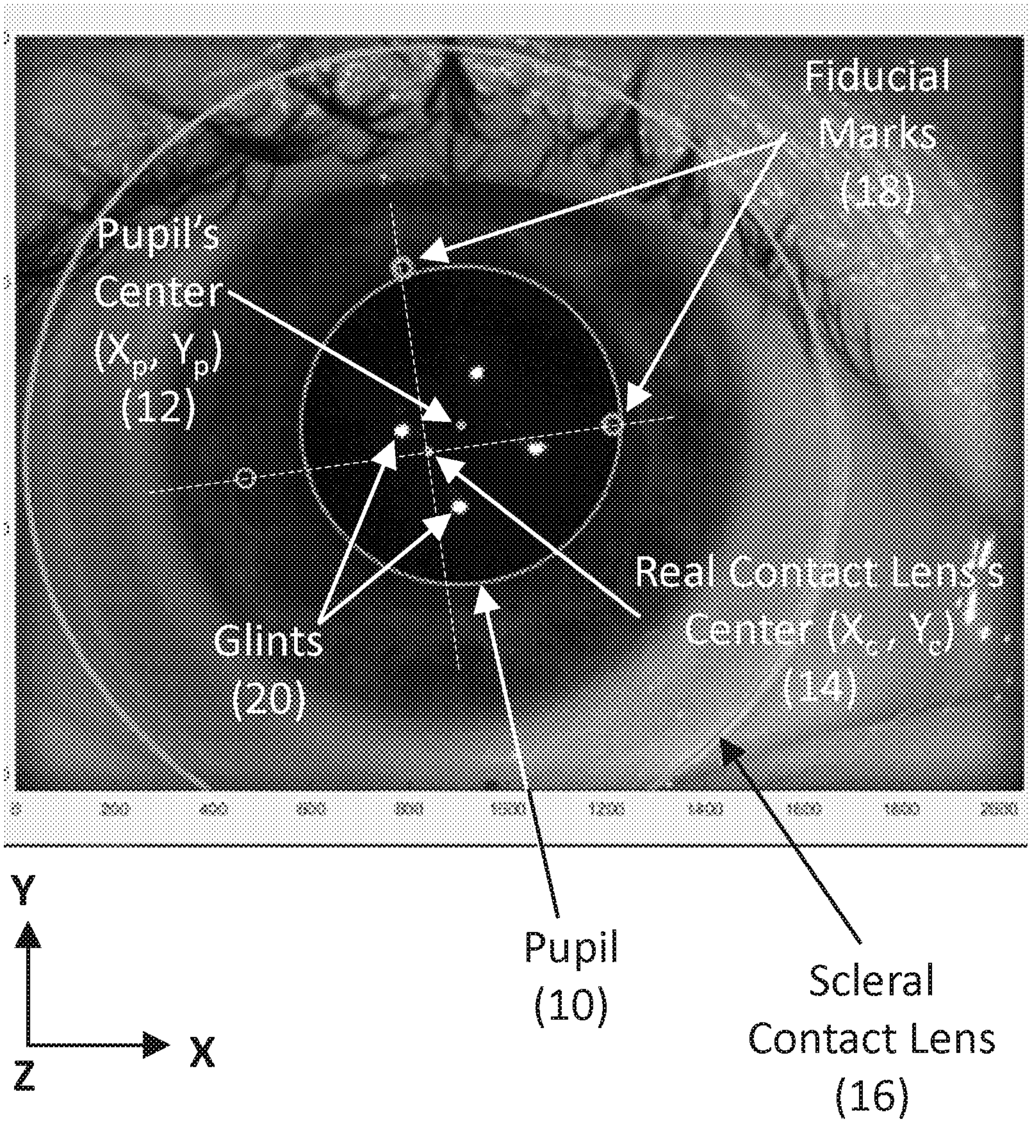
FIG. 1 shows a front view of an example of a visual image of an eye with a rotated and offset predicate scleral contact lens that has three fiducial marks, according to the present disclosure.

Disclosed herein is a method and system for determining the tilt(s) and XY offsets of a contact lens in order to determine the correct optical centration and rotation for manufacturing and fabricating wavefront-guided correction optics. There are several alternative embodiments that can be effective for this process.

The abbreviation "CL" means "Contact Lens". The abbreviation "EI" means "Eye Image". The abbreviation "CT" means "Corneal Topography". The term "Sag" means the sagittal height, $S_0$, of a contact lens. The terms "mis-centered" and "de-centered" and "offset" are all interchangeable, and they all refer to an $\Delta X$ and $\Delta Y$ offset of the contact lens in the XY plane from an eye's pupil center. The word "rotation" refers to a rotational angle, $\alpha$, of the contact lens around the Z-axis. The word "tilt" refers to the X- and Y-tilt angles ($\theta_x$ and $\theta_y$) of the contact lens around the X-axis and the Y-axis, respectively. A positive rotation is counter-clockwise, and a negative rotation is in the clockwise direction. The term "optimal location", as it refers to placement of a wavefront-guided correction patch on a wavefront-customized contact lens, means a calculated location where the Higher Order Aberrations (HOAs) (e.g., residual aberrations) of the patient's eye, when wearing a wavefront-customized contact lens, are minimized when the wavefront-guided correction patch is placed at the optimal XY location and to the optimal angular orientation. The word "normal", as it refers to a corneal or CL vertex, means a direction (e.g., vector) that is perpendicular to a tangent surface at a predefined point on the surface.

"The word "mismatched", as it refers to the position and rotation of a contact lens on an eye, means that the contact lens is misaligned with respect to the pupil of the eye. Therefore, a "mismatched" contact lens can have at least three possibilities: (1) a non-zero XY offset from the pupil's center, (2) a non-zero rotation angle, $\alpha$, wherein the vertical meridian of the CL doesn't align with the vertical Y-axis of the pupil, and (3) both a non-zero X and/or non-zero Y offset from the pupil's center and a non-zero rotation angle, $\alpha$, from the pupil's vertical Y-axis. Hence, a perfectly aligned contact lens would have a zero XY offset and a zero rotation angle, $\alpha$.

The term "aberrations" includes both Higher Order Aberrations (HOAs) and Lower Order Aberrations (LOAs) of a patient's eye. Standard predicate CLs can correct many LOAs, but not all aberrations. A wavefront-customized contact lens is designed to correct all aberrations, including both LOAs and HOAs. The word "normal" as it refers to a normal corneal contact lens includes both soft corneal contact lenses and rigid gas permeable (RGP) corneal contact lens. Scleral contact lenses are not normal contact lenses. Scleral lenses have a much larger diameter and significantly greater sagittal height, $S_0$, than normal corneal contact lenses. The words "correction patch" means a 2-dimensional wavefront map that is used to correct imperfections (i.e., aberrations) of an individual's eye.

FIG. 1 shows a front view of an example of a visual image of an eye with a rotated and offset predicate scleral contact lens 16 that has three fiducial marks 18 disposed thereon, according to the present disclosure. The scleral contact lens' real center 14 is offset by $\Delta X$ and $\Delta Y$ (in the XY plane) from the pupil center 12 of pupil 10. Also, four "glints" 20 are identified, which are Purkinje reflections from the corneal surfaces of a circular pattern of four illumination lights (at 0, 90, 180, and 270 degrees) around the Z-axis. In this example, the three fiducial marks 18 are placed in a 45/45/90 degree right isosceles triangular configuration.

Figure 2:
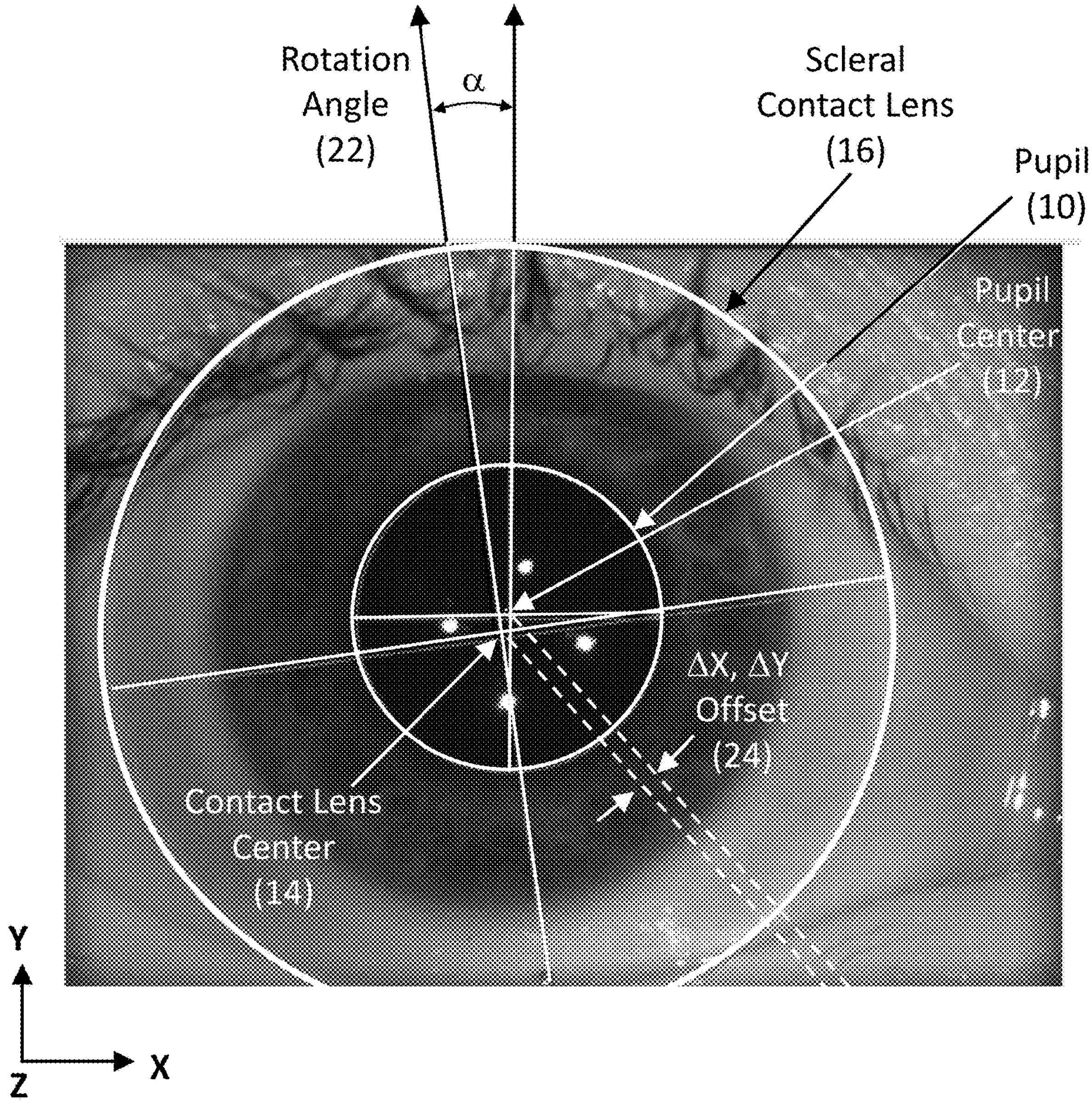
FIG. 2 shows a front view of an example of a visual image of an eye with a rotated and offset scleral contact lens without fiducial marks, according to the present disclosure.

FIG. 2 shows a front view of an example of a visual image of an eye with a rotated and offset scleral contact lens 16 (without fiducial marks,) according to the present disclosure. The real center 14 of the scleral contact lens 16 is offset 24 in the XY plane from the center 12 of pupil 10. The scleral contact lens 16 is also rotated around the Z-axis by a rotation angle 22, a. In this example, the amount of Z-axis rotation 22, $\alpha$, is approximately equal to +10 degrees and the amount of XY offset 24 is approximately equal to 1 mm. Four "glints" 20 can be seen, which are Purkinje reflections from the corneal surfaces of four illumination lights from an optical instrument (such as a wavefront aberrometer, or a corneal topographer, or a combined topographer/aberrometer instrument).

Figure 3:
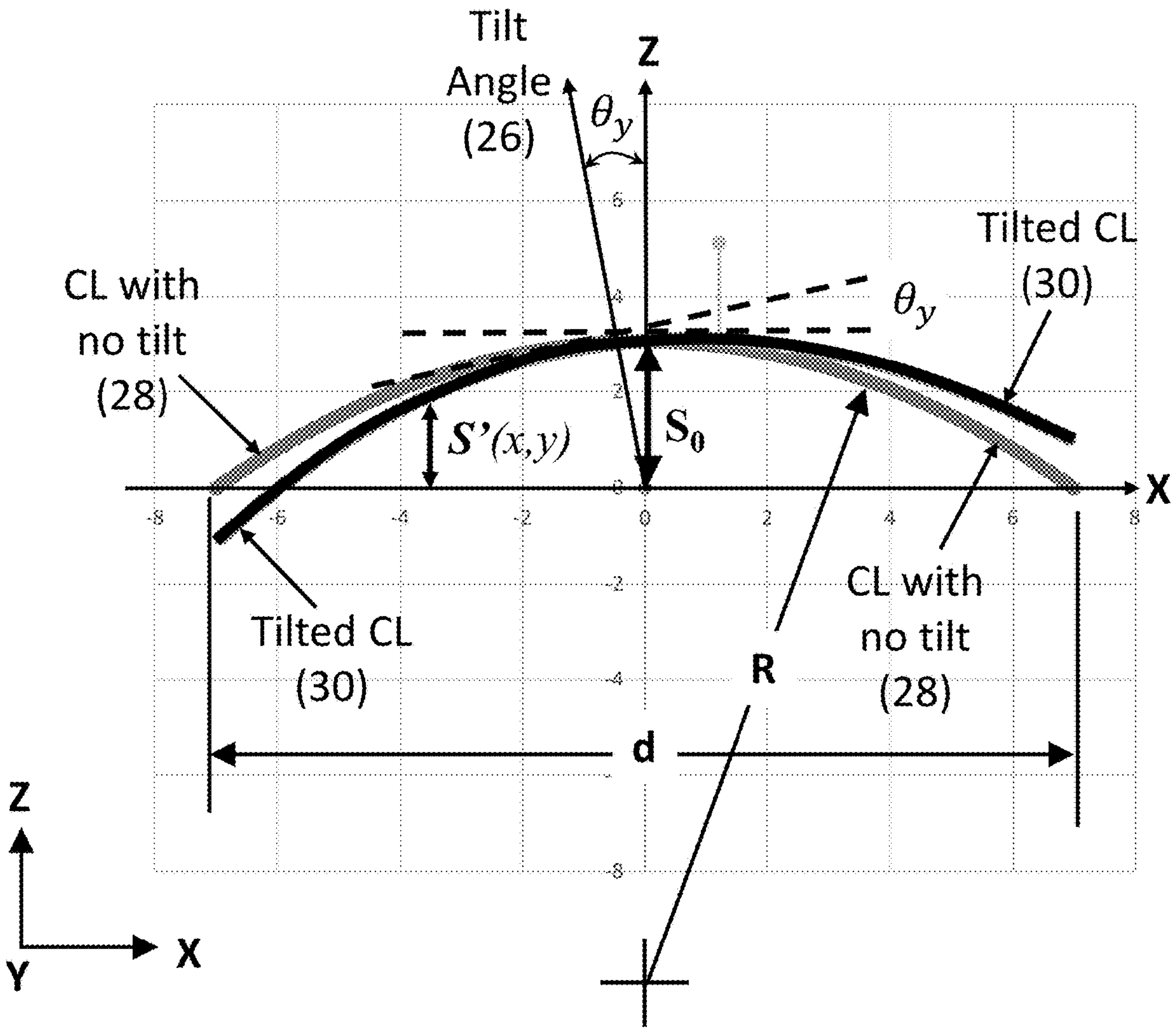
FIG. 3 shows a side cut-away view in the XZ plane of an example of tilted scleral contact lens compared to an example of a non-tilted scleral contact lens, according to the present disclosure.

FIG. 3 shows a side cut-away view in the XZ plane of an example of a tilted scleral contact lens 30 compared to an example of a non-tilted scleral contact lens 28, according to the present disclosure. The tilt angle 26 ($\theta_y$) in the XZ plane is identified. The sagittal height ("Sag"), $S_0$, of the scleral contact lens 28 is also shown. The radius of curvature, R, of scleral contact lens 28 (with no tilt) is shown, along with the diameter, d, of scleral contact lens 28 (with no tilt). S'(x,y) represents the vertical height in the Z-direction of tilted CL 30 at a specified (x,y) position.

Figure 4A:
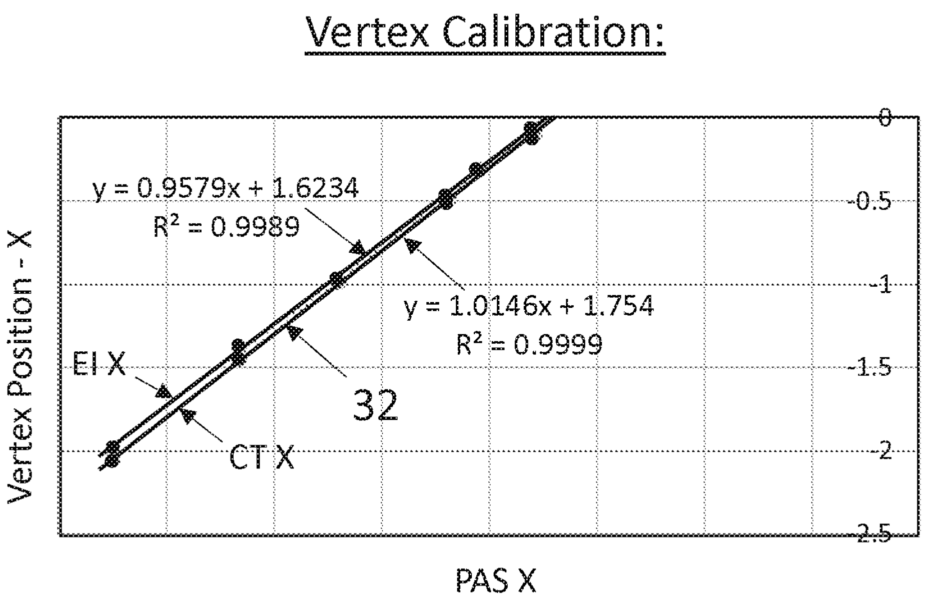
FIG. 4A shows a graph of an example of a Vertex Calibration of eye image (EI) measurements and corneal topography (CT) measurements of the X-component of the vertex location as a function of Position Alignment Stage (PAS X) position along the horizontal X-axis, according to the present disclosure.

FIG. 4A shows a graph of an example of a Vertex Calibration of eye image (EI) measurements and corneal topography (CT) measurements of the X-component of the vertex's location as a function of Position Alignment Stage ("PAS-X") location (i.e., optical instrument centration relative to the eye) along the horizontal X-axis, according to the present disclosure. The two different sets of measurements are in very close agreement with each other, and fall closely on a straight line 32, indicating a strong linear relationship between the movement of the aberrometer instrument in the X-direction (PAS-X) and the Vertex X-location (displayed on the Y-axis).

Figure 4B:
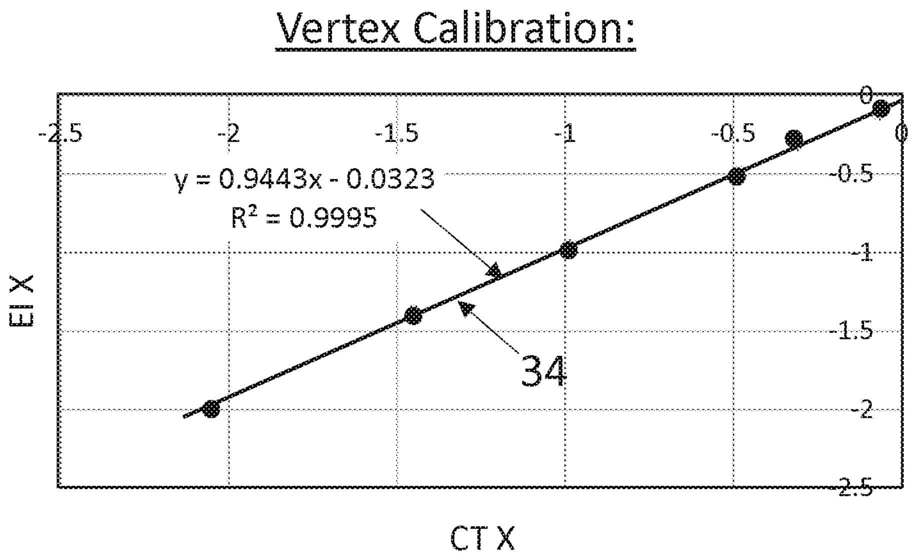
FIG. 4B shows a graph of an example of a Vertex Calibration showing a linear correlation between corneal topography (CT) measurements ("CT X" on the X-axis) and eye image (EI) measurements ("EI X" on the Y-axis), according to the present disclosure.

FIG. 4B shows a graph of an example of a Vertex Calibration showing a linear correlation between corneal topography (CT) measurements ("CT-X" on the horizontal X-axis) and eye image (EI) measurements ("EI-X" on the vertical Y-axis), according to the present disclosure. The EI-X measurements are about 5% underestimated, when compared to the CT-X measurements.

Figure 5:
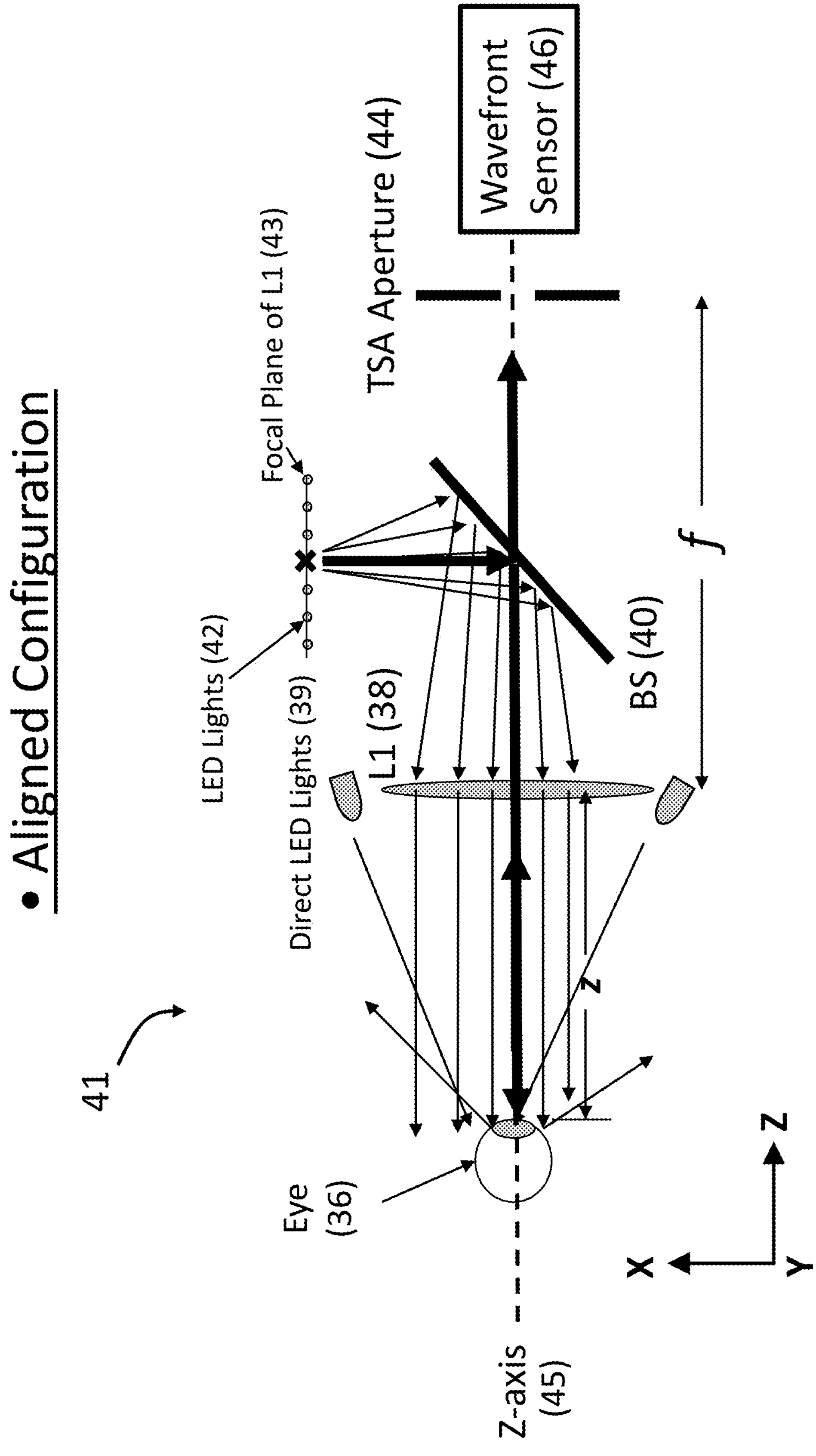
FIG. 5 shows a side view of a schematic example of a wavefront aberrometer instrument with an eye in an aligned configuration, according to the present disclosure.

FIG. 5 shows a side view of a schematic example of a wavefront aberrometer instrument 41 with an eye 36 in an aligned configuration, according to the present disclosure. Aberrometer instrument 41 comprises a front lens 38, a beamsplitter 40, a set of projected LED illumination lights 42 located at the focal plane 43 of front lens 38, a set of direct LED illumination lights 39 disposed circumferentially around the front lens 38, a Telecentric Stop Aperture (TSA) 44, and a wavefront sensor camera 46, wherein the beamsplitter 40 is disposed in-between the front lens 38 and the TSA 44. The TSA 44 is disposed in front of wavefront sensor camera 46 and is located in-between beamsplitter 40 and wavefront sensor camera 46. In this example, eye 36 is properly aligned with the main optical Z-axis 45.

In some embodiments, a corneal topographer instrument can be combined with an aberrometer instrument to make a combined topographer/aberrometer instrument.

Figure 6:
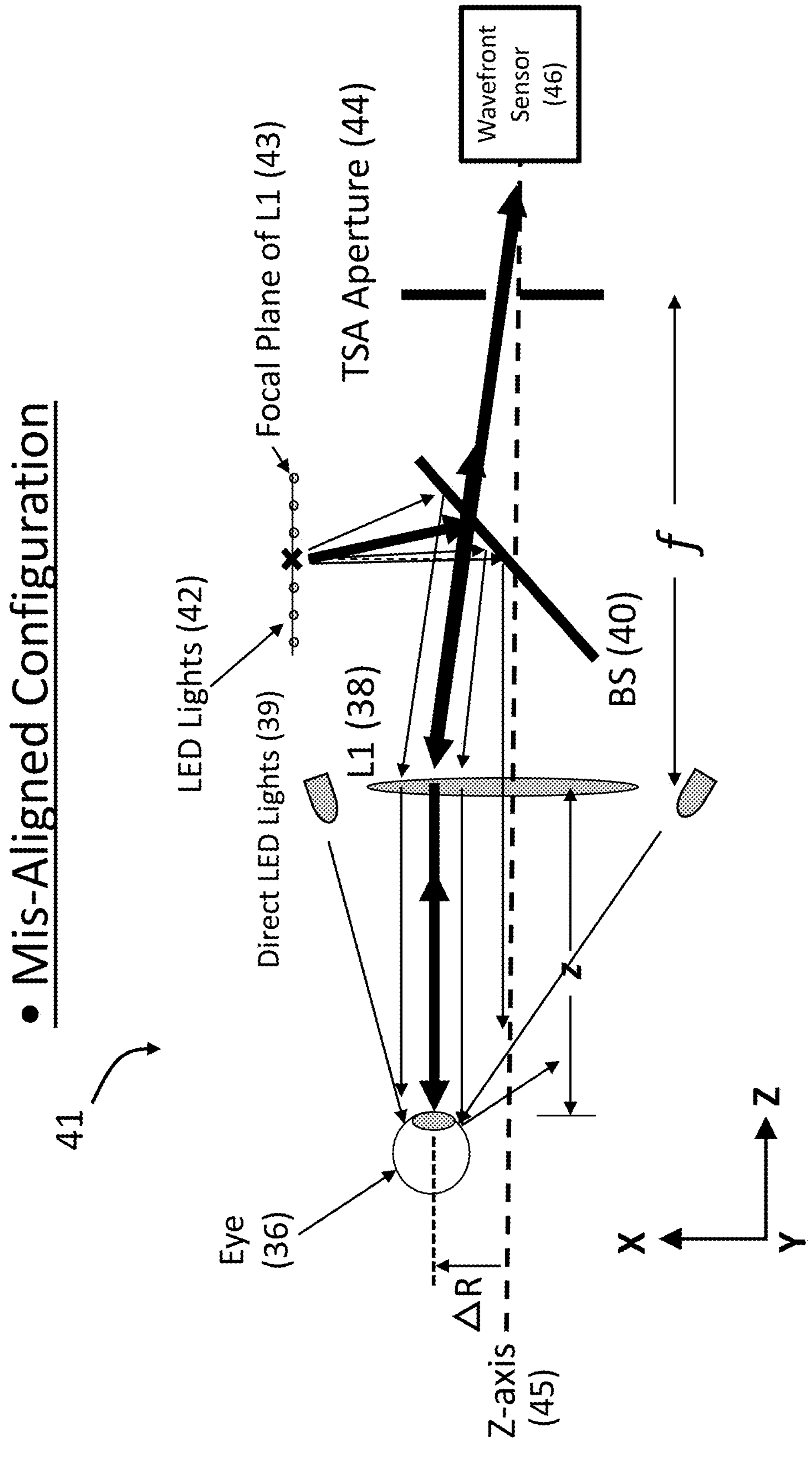
FIG. 6 shows a side view of a schematic example of a wavefront aberrometer instrument with an eye in a misaligned configuration, according to the present disclosure.

FIG. 6 shows a side view of a schematic example of a wavefront aberrometer instrument 41 with an eye 36 in a mis-aligned configuration, according to the present disclosure. Aberrometer instrument 41 comprises a front lens 38, a beamsplitter 40, a set of projected LED illumination lights 42 located at the focal plane 43 of front lens 38, a set of direct LED illumination lights 39 disposed circumferentially around the front lens 38, a TSA 44, and a wavefront sensor camera 46, wherein the beamsplitter 40 is disposed in-between the front lens 38 and the TSA 44. The TSA 44 is disposed in front of wavefront sensor camera 46 and is located in-between beamsplitter 40 and wavefront sensor camera 46. In this example, eye 36 is mis-aligned radially by a radial distance=$\Delta$R from the main optical Z-axis 45.

Figure 7:
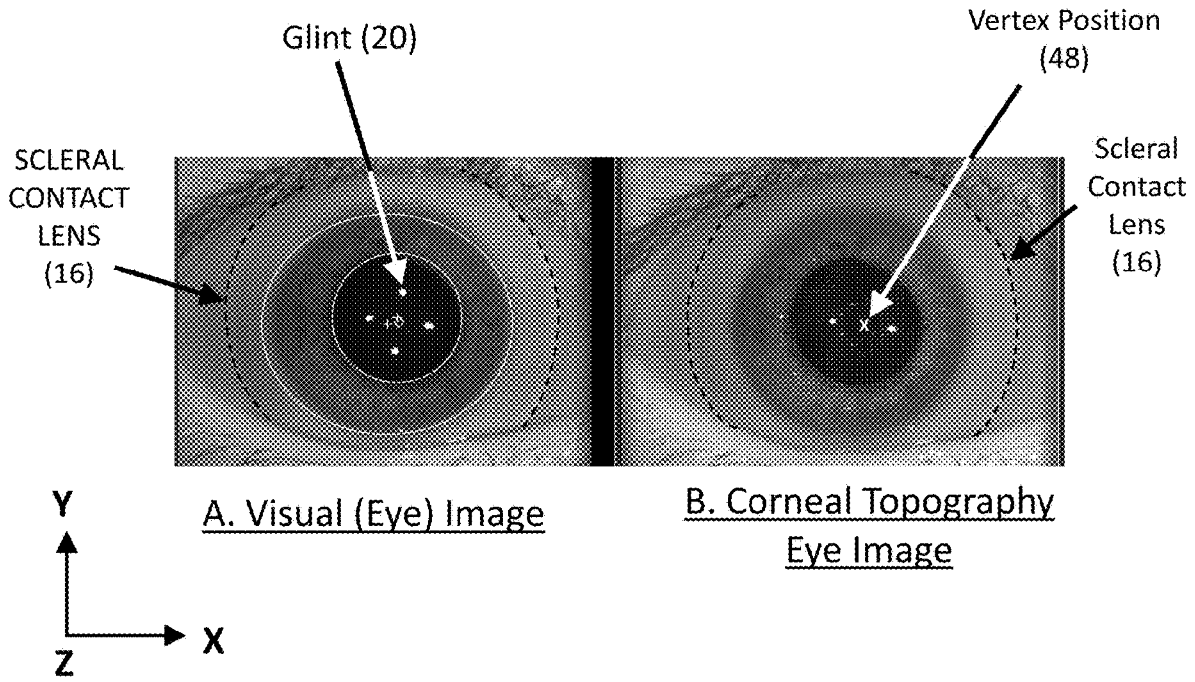
FIG. 7 shows a front view of an example of a comparison of a visual image of an eye (A) and a corneal topography image of the same eye (B), according to the present disclosure.

FIG. 7 shows a front view of an example comparing a visual image of an eye (A) and a corneal topography image of the same eye (B), according to the present disclosure. The edge of scleral contact lens 16 is identified, as well as glint 20. A corneal vertex position 48 is shown in the corneal topography image (B).

Figure 8:
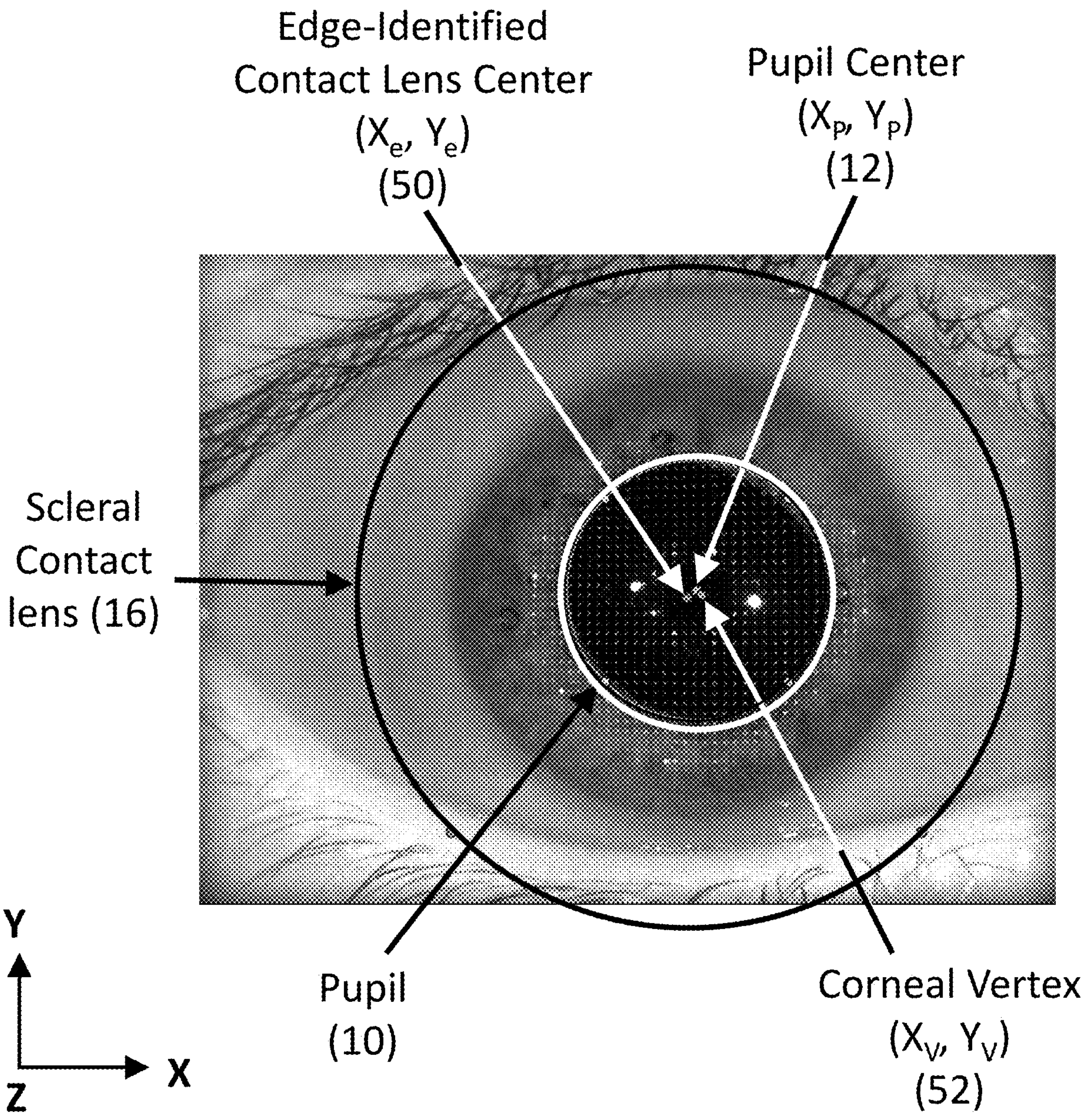
FIG. 8 shows a front view of an example of a corneal topographic image of an eye with an offset predicate scleral contact lens, according to the present disclosure.

FIG. 8 shows a front view of an example of a corneal topography image of an eye with an offset predicate scleral contact lens, according to the present disclosure. The pupil center 12 ($X_p$, $Y_p$) of pupil 10, the corneal vertex 52 ($X_v$, $Y_v$), and the edge-identified scleral CL center 50 ($X_e$, $Y_e$) of scleral contact lens 16 are illustrated. In this example, none of these three different centers line up with each other, and they are offset from each other in the XY plane.

Figure 9:
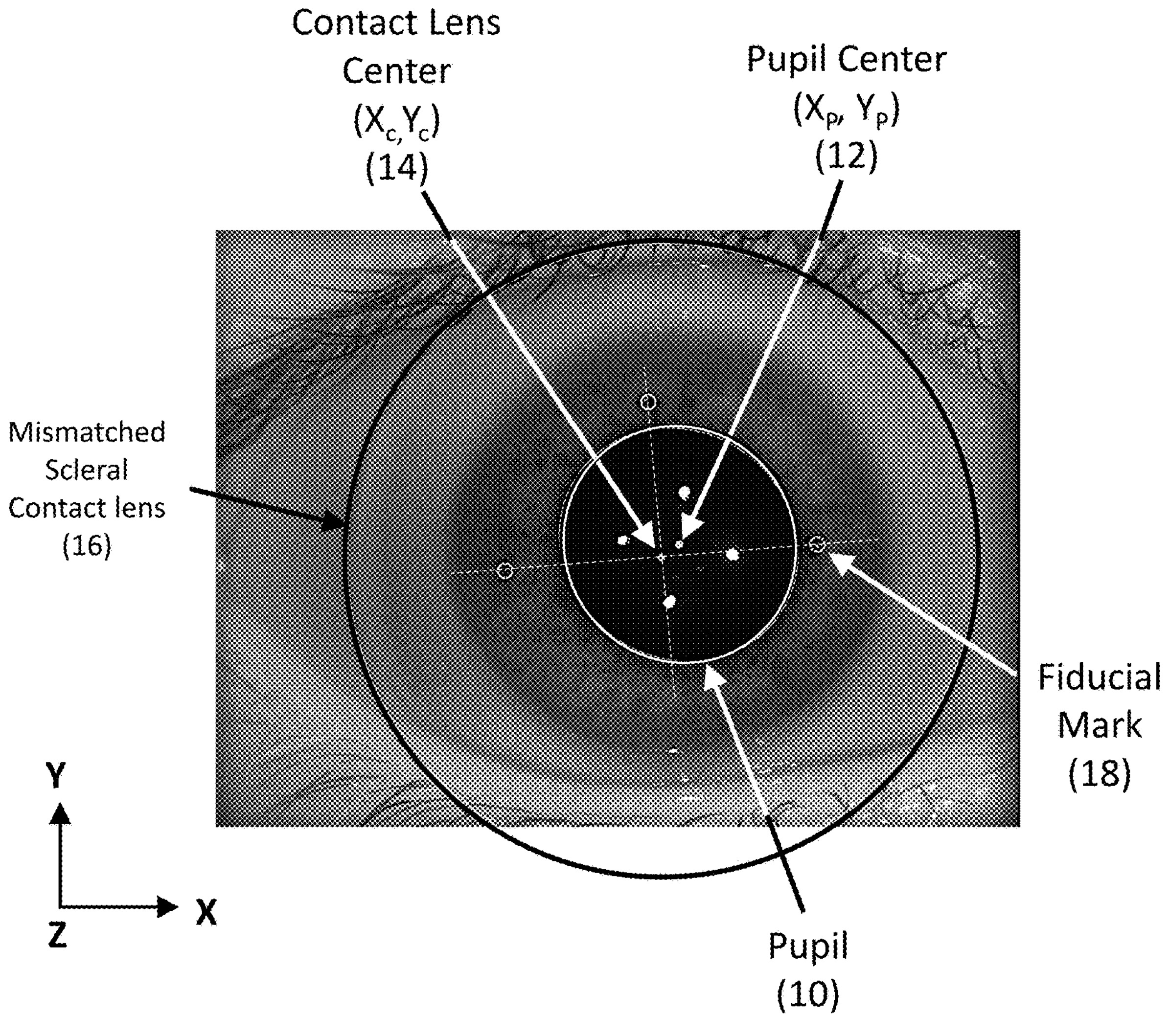
FIG. 9 shows a front view of an example of a visual image of an eye with an offset predicate scleral contact lens, according to the present disclosure.

FIG. 9 shows a front view of an example of a visual image of an eye with an offset (mismatched) predicate scleral contact lens 16, with three fiducial marks 18 arranged outside of pupil 10, according to the present disclosure. The pupil center 12 ($X_p$, $Y_p$) of pupil 10 and the real CL center 14 ($X_c$, $Y_c$) of scleral contact lens 16 are identified, where the real CL center 14 is determined from the three fiducial marks 18 (see dashed orthogonal lines).

Figure 10:
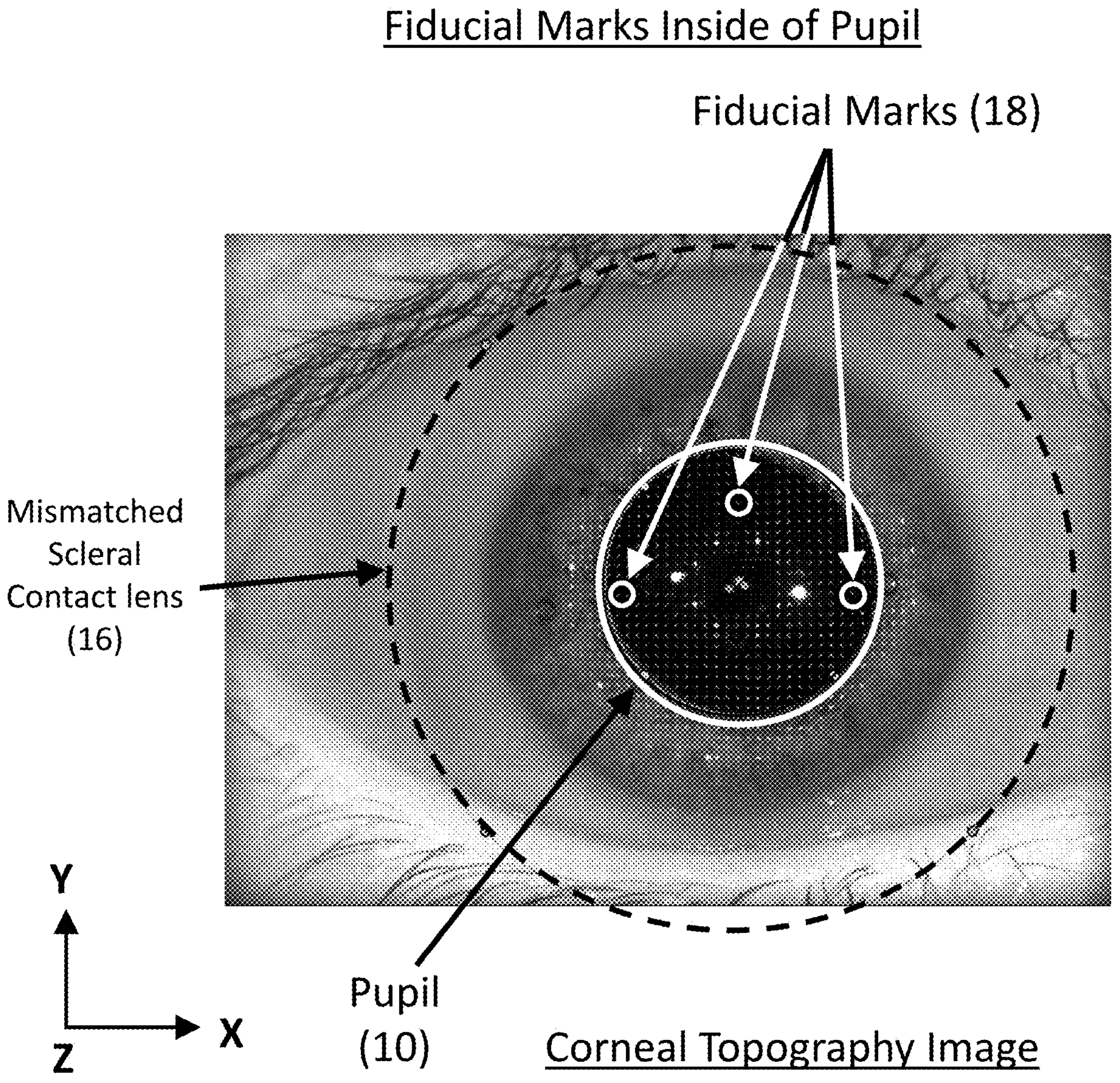
FIG. 10 shows a front view of an example of a corneal topography eye image of a predicate scleral contact lens with three fiducial marks that are located inside of the pupil, according to the present disclosure.

FIG. 10 shows a front view of an example of a corneal topography image of an eye with three fiducial marks 18 disposed on a mismatched predicate scleral contact lens 16 that are located inside of pupil 10, according to the present disclosure.

Figure 11:
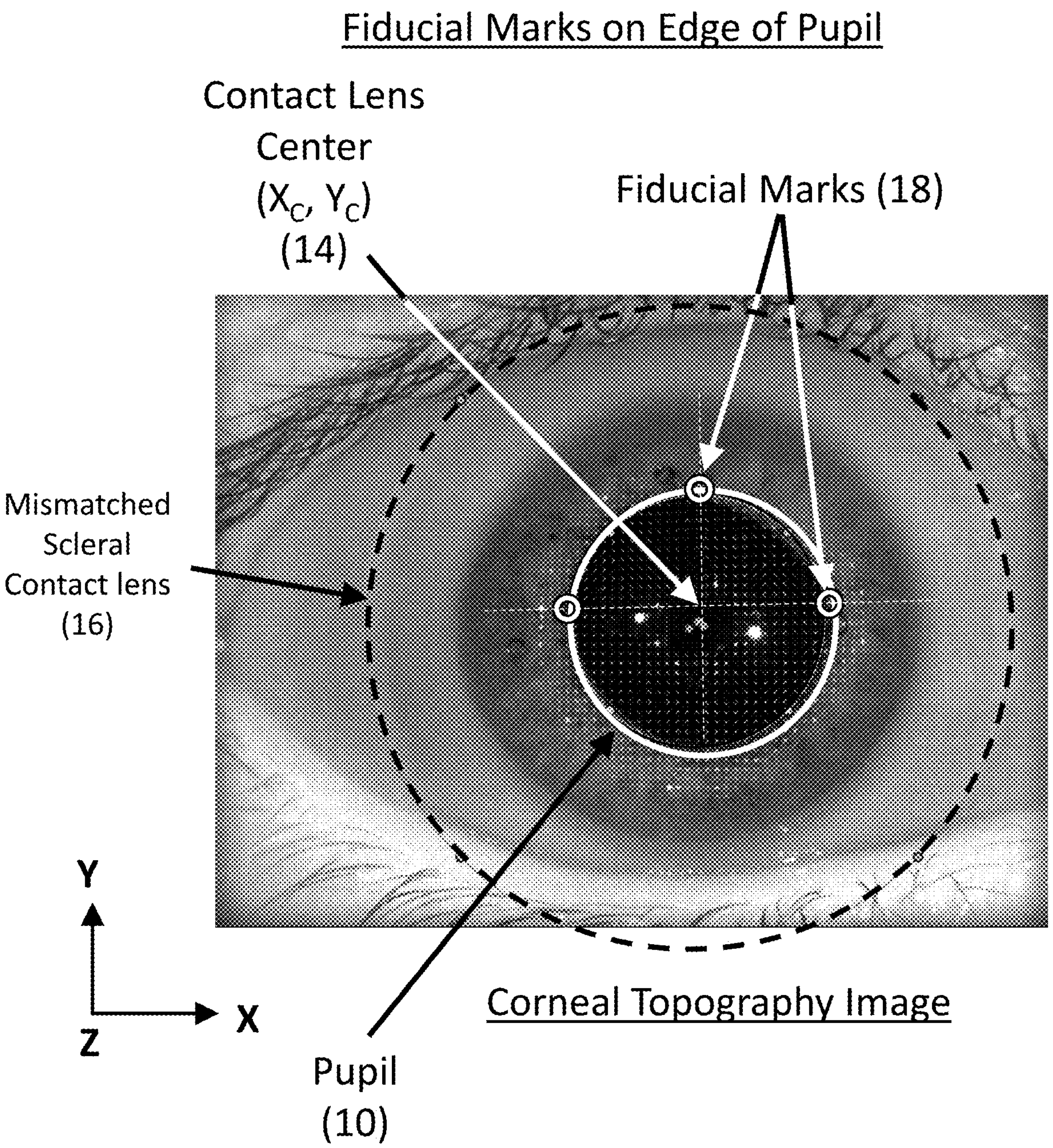
FIG. 11 shows a front view of an example of a corneal topography image of an eye with three fiducial marks on a predicate scleral contact lens that are located on the edge of the pupil, according to the present disclosure.

FIG. 11 shows a front view of an example of a corneal topography image of an eye with three fiducial marks 18 that are located on the edge of pupil 10, according to the present disclosure. Real CL center 14 can be identified from the position of the three fiducial marks 18, and mismatched CL edge obtained from real CL center 14 and predefined CL diameter d.

A first embodiment of a method of use (i.e., Method A) is to locate one or more fiducial marks 18 on a predicate contact lens 16 in locations away from the edge of the predicate contact lens 16 and nearer to the CL's physical center 14. This will minimize the impact of contact lens tilt, and the real CL center 14 can be measured from the predefined fiducial marks 18.

Method A provides a straightforward approach to identify the real physical CL center ($X_c$, $Y_c$) and calculate the XY offset ($\Delta$X, $\Delta$Y) and rotation angle $\alpha$ of a contact lens that is displaced away from the optical center of the eye ($X_P$, $Y_P$). This determination allows an optical diagnostician to properly place the correcting optics (e.g., a wavefront-guided correction patch) on contact lens 16 to make a wavefront-customized contact lens (not shown). Fiducial marks 18 may be positioned in a region where they might overlap with the pupil and thereby degrade the optical quality of the optical zone. Even if they could be placed outside the pupil, to be centrally placed they are, by necessity, located in front of the iris. Iris structure(s) then makes these more difficult to see and potentially creates difficulties with image processing. Hence, in some embodiments, the positions of fiducial marks 18 can be located on the edge of the pupil 10, or inside of the pupil 10 (See, for example, FIGS. 10 and 11).

Method B comprises measuring a tilt and offset of the contact lens directly with an aberrometer optical instrument. If a location on the contact lens that is normal to the optical Z-axis of the aberrometer can be determined, then the real CL center ($X_c$, $Y_c$) can be obtained by quantifying the tilt of the contact lens. It starts with measuring the virtual CL center ($X_e$, $Y_e$) from the image processing technique and lens diameter and edge information, by using the following equations, as follows:

$$X_e = (X_{edge1} + X_{edge2})/2 \text{ and} \tag{Eq. 1}$$

$$Y_e = (Y_{edge1} + Y_{edge2})/2, \tag{Eq. 2}$$

where $X_{edge1}$, $X_{edge2}$, $Y_{edge1}$, and $Y_{edge2}$ are measured directly from a visual image of the eye using edge detection software algorithms.

The surface S(x,y) of a spherical contact lens, especially inside an optical zone of the CL, can be approximated by the lens surface radius of curvature, R, as follows:

$$S(x, y) = S_0 - \frac{x^2}{2R} + \frac{y^2}{2R} \tag{Eq. 3}$$

where:

$$S_0 = \frac{\left(\frac{d}{2}\right)^2}{2R}. \tag{Eq. 4}$$

In equations (3) and (4), "d"=diameter of the contact lens, R=radius of curvature of the contact lens, and $S_0$=sagittal height of the contact lens. The tilted CL surface, S'(x,y), is defined by the coordinate transformation for each X- and Y-meridian, according to:

$$\begin{bmatrix} x' \\ S' \end{bmatrix} = \begin{bmatrix} \cos\theta_x & -\sin\theta_x \\ \sin\theta_x & \cos\theta_x \end{bmatrix} \begin{bmatrix} x \\ S \end{bmatrix} \tag{Eq. 5}$$

And, similarly for the Y-meridian:

$$\begin{bmatrix} y' \\ S' \end{bmatrix} = \begin{bmatrix} \cos\theta_y & -\sin\theta_y \\ \sin\theta_y & \cos\theta_y \end{bmatrix} \begin{bmatrix} y \\ S \end{bmatrix} \tag{Eq. 6}$$

These two coordinate transformations define the surface, S'(x,y), of a new tilted CL surface that is tilted by angles $\theta_x$ and $\theta_y$.

The location of the corneal vertex normal (which is perpendicular to the cornea's surface at the cornea's center) can be determined optically from centroid measurements of two or more (e.g., four) Purkinje reflections of a visual eye image (EI) in FIG. 7 ("glints", see image A on left side). Alternatively, when a telecentric corneal topography (CT) eye image (see image B in FIG. 7 on right side) is accessible, the vertex ($X_v$, $Y_v$) can be obtained from the CT eye image with the small "X" on the right side which is the location of a vertex point. Determining vertex center coordinates ($X_v$, $Y_v$) from a telecentric CT measurements is an accurate process. One property of telecentricity is that even as the eye is misaligned in a radial direction perpendicular to the main optical Z-axis, the central vertex image remains the true corneal vertex. Determining the vertex center from EI measurements requires performing a calibration. FIGS. 4A and 4B show examples of a vertex calibration (i.e., the X-component of the vertex's position) for comparing results of EI measurements to CT measurements, with a resulting maximum error of about 5%. The resulting vertex calibration response is very linear and predictable and has an acceptable accuracy.

In addition, the contact lens virtual (edge-identified) center ($X_e$, $Y_e$) can be determined by fitting the contact lens' edge definition to a circle (or ellipse). From these operations, the virtual contact lens center ($X_e$, $Y_e$) and the corneal vertex location ($X_v$, $Y_v$) can be determined. The lens' tilt angles ($\theta_x$ and $\theta_y$) are thus given by:

$$\theta_x = \tan^{-1}\frac{X_v - X_e}{R} \tag{Eq. 7}$$

$$\text{and } \theta_y = \tan^{-1}\frac{Y_v - Y_e}{R}. \tag{Eq. 8}$$

The following pair of equations define the real center ($X_c$, $Y_c$) of the tilted contact lens, as follows:

$$X_c = X_e + S_0\sin\theta_x \text{ and} \tag{Eq. 9}$$

$$Y_c = Y_e = S_0\sin\theta_y. \tag{Eq. 10}$$

There are several ways to make the measurement of the corneal vertex position with a contact lens on the eye. In nearly all aberrometers there is also a system for visually imaging the iris of the eye with a camera. This is the system that is generally used to determine the alignment of the contact lens on the eye during the measurement through the aberrometer instrument's front lens. The illumination of the eye is often made using one or more front light sources (usually LEDs) that are arranged circumferentially around the front camera lens. Since the eye and contact lens are both highly curved convex surfaces, there will always be a Purkinje reflection (glint) from these surfaces that is visible in the camera's visual image. These reflections can be used as a means for finding the position of the surface that is normal to the measurement axis. Note that this method depends on the exact arrangement of the imaging optical system, and thus the contact lens vertex position is related to the center of the pattern of Purkinje reflection spots (i.e., glints).

However, if the eye (and hence the cornea) moves radially away from the main optical axis (Z-axis) of the imaging system (See FIG. 6), then this creates an increasing amount of error because the LED sources reflect off different portions of the spherical cornea. This error is very systematic, and a calibration can be used to make a useful correction.

When fiducial marks 18 are located inside a dilated (larger) pupil, they might not be able to be distinguished from a visible iris image (it is not consistent; sometimes we can, and sometimes we cannot). Instead, they can always be easily found in the WFS (Wavefront Sensor) image taken by an aberrometer instrument.

In some embodiments, one or more fiducial marks 18 can be located on a predicate CL 16: ($\alpha$) outside of the pupil, but inwards from the edge of the CL 16 (see FIG. 9), (b) inside of the pupil 10 (see FIG. 10), or (c) at the edge of the pupil 10 (see FIG. 11).

In some embodiments, three fiducial marks can be used on a predicate CL, which can be arranged in an isosceles triangle configuration (see, for example, FIGS. 9, 10, and 11).

In a combined corneal topographer and aberrometer instrument, a part of the light is projected through the collecting lens and is collimated by a Telecentric Stop Aperture (TSA) so that the only rays collected in object space are parallel to the instrument's Z-axis. This is shown in FIGS. 5 and 6. In this case, the position of the vertex tangent surface that is normal to the instrument optical axis is independent of the eye's radial misalignment, ΔR.

In some embodiments, the following equations (11, 12, 13, and 14) can be used to calculate the XY offset amounts (ΔX, ΔY) between the physical center ($X_c$, $Y_c$) of the tilted and/or rotated predicate contact lens and the center of the pupil ($X_p$, $Y_p$), as follows:

$$L = \sqrt{(X_P - X_c)^2 + (Y_P - Y_c)^2} \quad \text{(Eq. 11)}$$

$$\phi = \tan^{-1}\left(\frac{Y_P - Y_c}{X_P - X_c}\right) \quad \text{(Eq. 12)}$$

$$\Delta X = L\cos(\phi - \alpha) \quad \text{(Eq. 13)}$$

$$\Delta Y = L\sin(\phi - \alpha). \quad \text{(Eq. 14)}$$

$$\text{Also, } \Delta X' = X_p - X_c \quad \text{(Eq. 15)}$$

$$\Delta Y' = Y_p - Y_c. \quad \text{(Eq. 16)}$$

Figure 12:
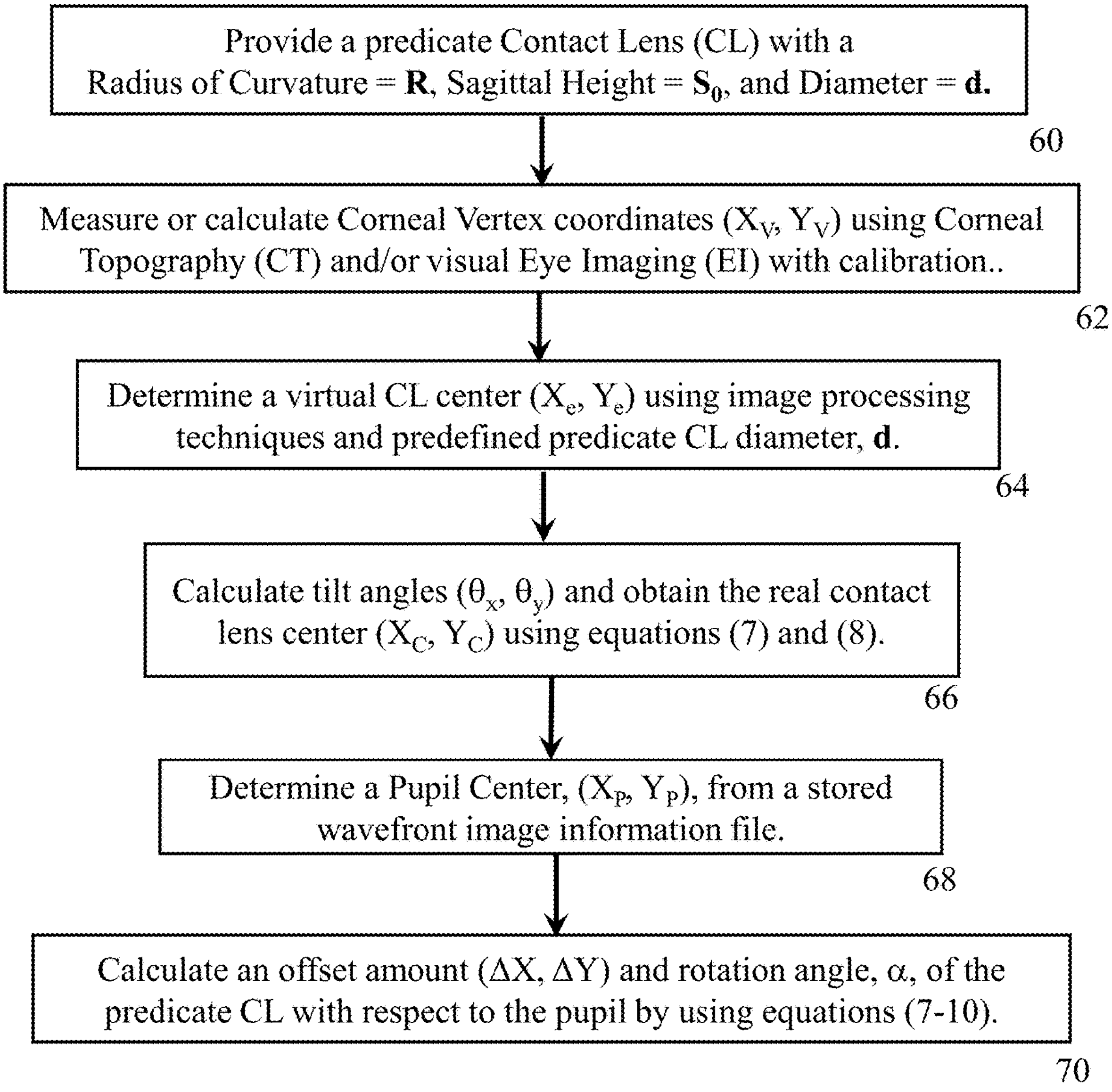
FIG. 12 is an example of a process flow chart illustrating sequential method steps for calculating the XY offset ($\Delta X$, $\Delta Y$) of a contact lens that is displaced from the optical center of the eye, according to the present disclosure.

FIG. 12 shows an example of a process flow chart illustrating sequential method steps for calculating the XY offset (ΔX, ΔY) of a contact lens that is displaced away from the optical center of the eye, according to the present disclosure. Firstly, step 60 comprises providing a predicate Contact Lens (CL) with a known Radius of Curvature=R, Sagittal height=$S_0$, and Diameter=d. Next, step 62 comprises measuring or calculating Corneal Vertex coordinates ($X_v$, $Y_v$) using CT or visual EI techniques with calibration. Next, step 64 comprises determining a virtual CL center ($X_e$, $Y_e$) using image processing techniques and predefined CL diameter, d. Next, step 66 comprises calculating tilt angles ($\theta_x$, $\theta_y$) and obtaining the real contact lens center ($X_C$, $Y_C$) using equations (7) and (8). Next, step 68 comprises determining the Pupil Center ($X_p$, $Y_p$), from the wavefront sensor's imaging intensity information and with specialized wavefront sensor image processing techniques, using a stored wavefront information file. Finally, step 70 comprises calculating a XY offset amount (ΔX, ΔY) and a rotation angle, α, of the predicate CL with respect to the pupil center by using equations (7-10). This example of a method can be applied to either a corneal CL or a scleral CL.

Figure 13:
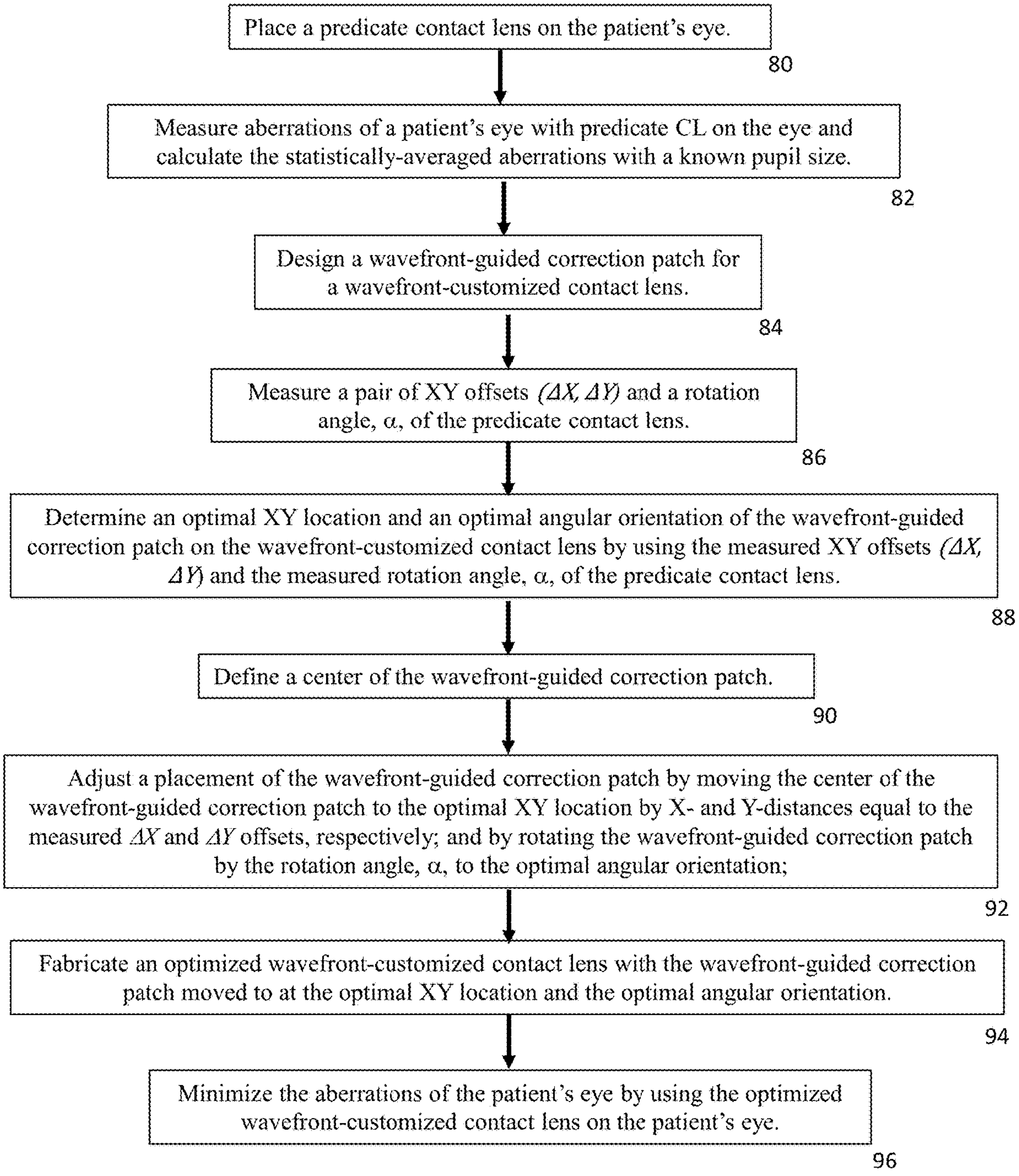
FIG. 13 is an example of a process flow chart illustrating sequential method steps for minimizing residual Higher Order Aberrations (HOAs) of the patient's eye by fabricating and using an optimized wavefront-customized contact lens on the patient's eye, according to the present disclosure.

FIG. 13 shows an example of a process flow chart illustrating sequential method steps for minimizing aberrations of the patient's eye by fabricating and using an optimized wavefront-customized contact lens on the patient's eye, according to the present disclosure. Firstly, step 80 comprises placing a predicate contact lens on the patient's eye. Next, step 82 comprises measuring aberrations of a patient's eye with predicate CL on the eye and calculating the statistically averaged aberrations with a known pupil size. Next, step 84 comprises designing a wavefront-guided correction patch for a wavefront-customized contact lens. Next, step 86 comprises measuring a pair of XY offsets (ΔX, ΔY) and a rotation angle, α, of the predicate contact lens. Next, step 88 comprises determining an optimal XY location and an optimal angular orientation of the wavefront-guided correction patch on the wavefront-customized contact lens by using the measured pair of XY offsets (ΔX, ΔY) and the measured rotation angle, α, of the predicate contact lens. Next, step 90 comprises defining a center of the wavefront-guided correction patch. Next, step 92 comprises adjusting a placement of the wavefront-guided correction patch on a contact lens by: (1) placing the center of the wavefront-guided correction patch to the optimal XY location using the measured pair of ΔX and ΔY offsets, and (2) rotating the wavefront-guided correction patch to the optimal angular orientation by using the rotation angle, α. Next, step 94 comprises fabricating an optimized wavefront-customized contact lens by positioning the wavefront-guided correction patch at the optimal XY location and the optimal angular orientation. Finally, step 96 comprises minimizing the aberrations of the patient's eye by using the optimized wavefront-customized contact lens on the patient's eye. This example of a method can be applied to either a corneal CL or a scleral CL.

Figure 14:
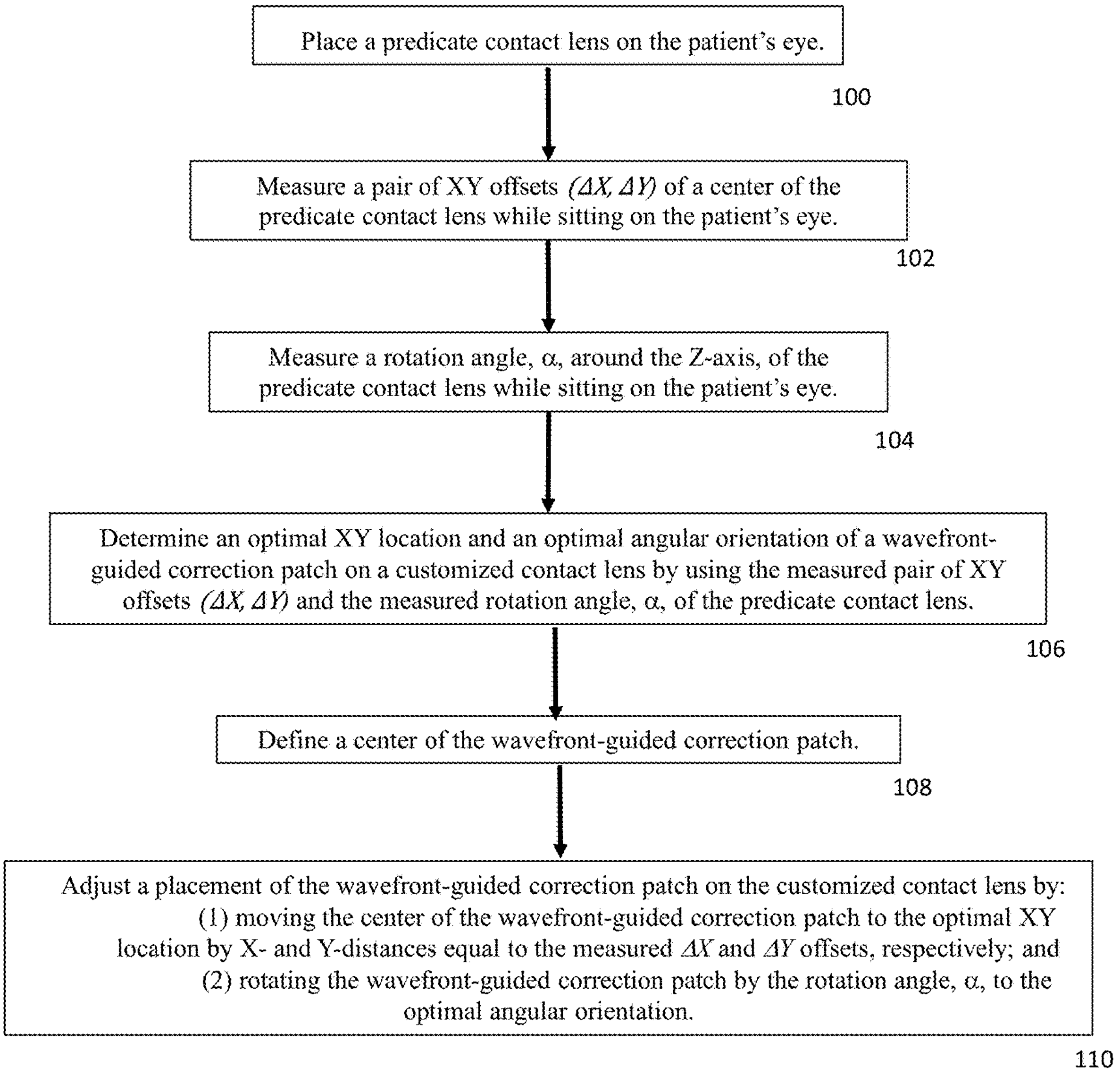
FIG. 14 is an example of a process flow chart illustrating sequential method steps for correcting aberrations of a patient's eye with a customized contact lens.

FIG. 14 shows an example of a process flow chart illustrating sequential method steps for correcting aberrations of a patient's eye with a customized contact lens, wherein the method comprises performing the following steps. Firstly, step 100 comprises placing a predicate contact lens on the patient's eye. Next, step 102 comprises measuring a pair of XY offsets (ΔX, ΔY) of a center of the predicate contact lens, while sitting on the patient's eye. Next, step 104 comprises measuring a rotation angle, α, of the predicate contact lens, while sitting on the patient's eye. Next, step 106 comprises determining an optimal XY location and an optimal angular orientation of a wavefront-guided correction patch on the customized contact lens by using the measured pair of XY offsets (ΔX, ΔY) and the measured rotation angle, α, of the predicate contact lens. Next, step 108 comprises defining a center of the wavefront-guided correction patch. Finally, step 110 comprises adjusting a placement of the wavefront-guided correction patch on the customized contact lens by: (1) placing the center of the wavefront-guided correction patch to the optimal XY location by X- and Y-distances equal to the measured ΔX and ΔY offsets, respectively; and by (2) rotating the wavefront-guided correction patch by the rotation angle, α, to the optimal angular orientation. This example of a method can be applied to either a corneal CL or a scleral CL.

Figure 15:
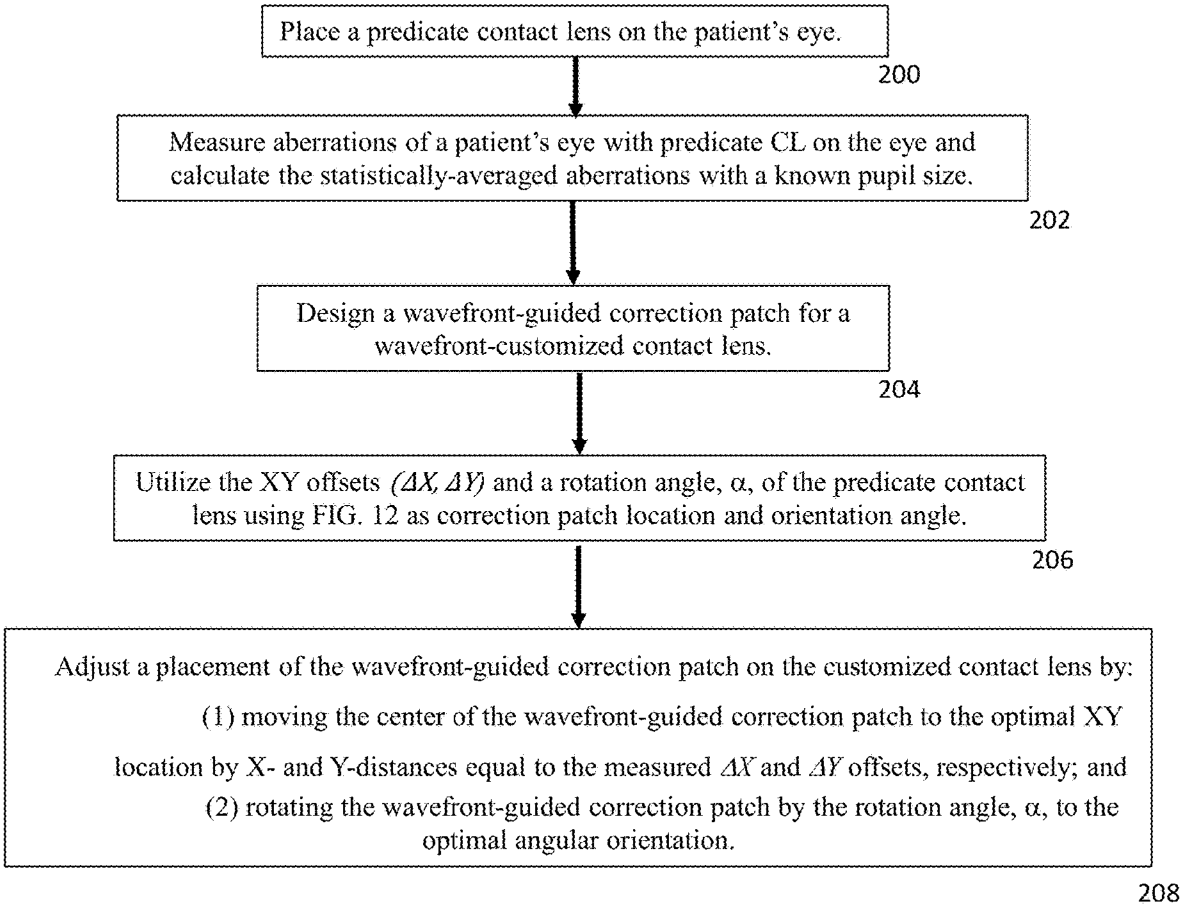
FIG. 15 is an example of a process flow chart illustrating sequential method steps for correcting aberrations of a patient's eye with a customized contact lens.

FIG. 15 shows an example of a process flow chart illustrating sequential method steps for minimizing aberrations of the patient's eye, especially Higher Order Aberrations (HOAs), by fabricating and using an optimized wavefront-customized contact lens on the patient's eye, according to the present disclosure. The method of aberrations of a patient's eye can comprise performing the following steps. Firstly, step 200 comprises placing a predicate contact lens on the patient's eye. Next, step 202 comprises measuring aberrations of a patient's eye with the predicate CL on the eye by using an aberrometer and calculating statistically averaged aberrations (i.e., averaged over time) for a known pupil size. Next, step 204 comprises designing a wavefront-guided correction patch for a wavefront-customized contact lens by using the calculated aberration of the patient's eye. Next, step 206 comprises utilizing the XY offsets (ΔX, ΔY)

and a rotation angle, α, of the predicate contact lens from FIG. 12 as correction patch location and orientation angle. Next, step 208 comprises adjusting a placement of the wavefront-guided correction patch on the customized contact lens by: (1) placing the center of the wavefront-guided correction patch on the optimal XY location by X- and Y-distances equal to the measured ΔX and ΔY offsets, respectively; and by (2) rotating the wavefront-guided correction patch by the rotation angle, α, to the optimal angular orientation. This example of a method can be applied to either a corneal CL or a scleral CL.

The XY location of vertex central point ($X_v$, $Y_v$) can be obtained from either a calibrated EI image (e.g., centroid of the four glints) or from a true vertex location from a telecentric CT image. In the telecentric corneal topographer, an exact vertex location can be directly determined. Determining ($X_v$, $Y_v$) from EI measurements requires performing a calibration (see FIGS. 4A and 4B).

Methods A and B comprise two different approaches to obtain the real CL center ($X_c$, $Y_c$), while EI and CT measurements comprise two different ways to find the vertex central point ($X_v$, $Y_v$).

Figure 16:
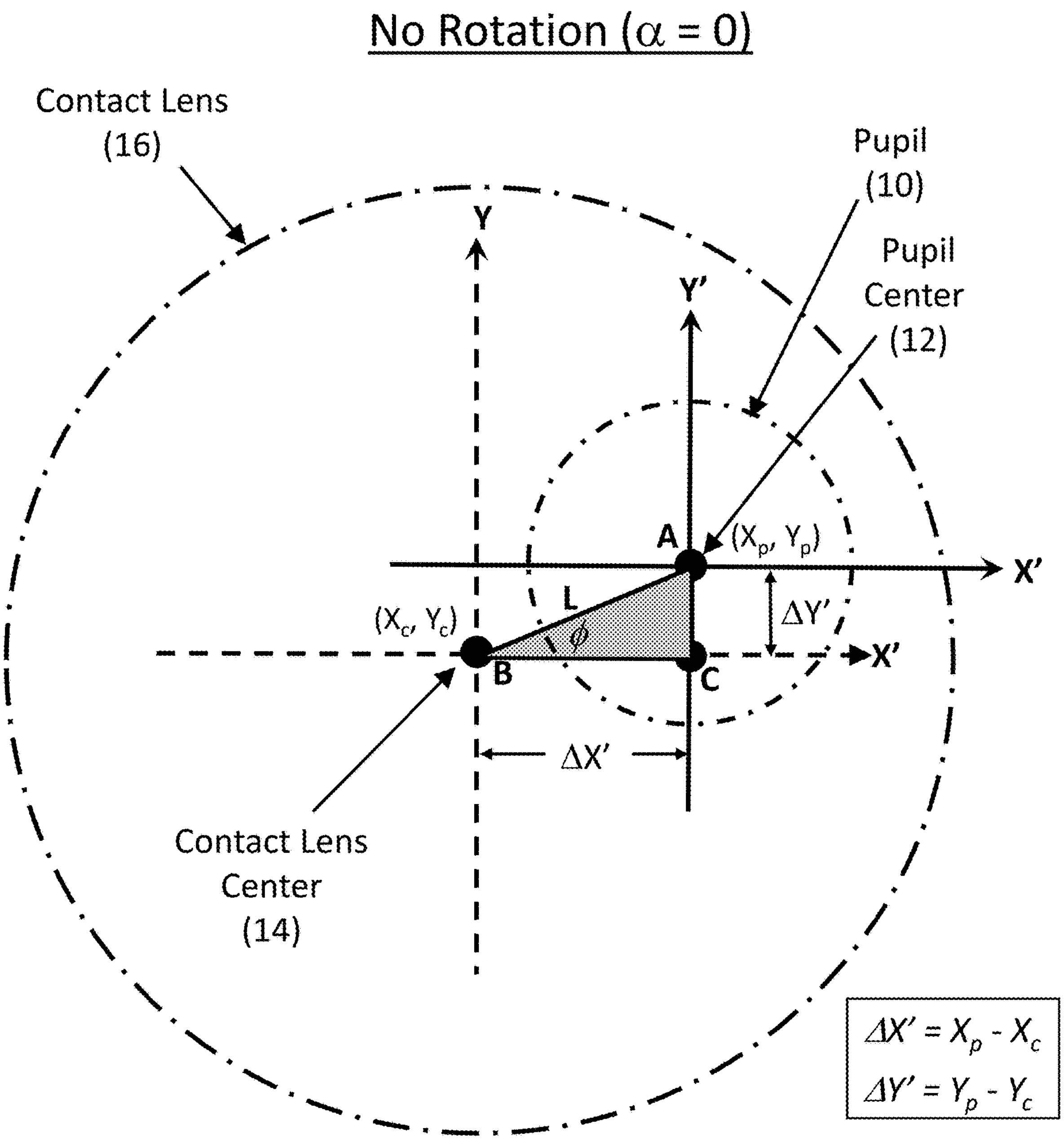
FIG. 16 shows a schematic example of a geometric layout of a pupil and a contact lens that is offset in the XY plane from the center of the pupil, with zero rotational angle, $\alpha$, according to the present disclosure.

FIG. 16 shows a schematic example of a geometric layout of pupil 10 and contact lens 16 that is offset in the XY plane from pupil 10, with a zero rotational angle, α, according to the present disclosure. Note that the amount of XY offset is exaggerated in this Figure to better illustrate the geometrical relationships among the different geometries. Two different coordinate systems are used: XY coordinates for the contact lens 16, and X'Y' coordinates for the pupil 10. This figure shows the geometric relationship between pupil center 12 of pupil 10 and contact lens center 14 of contact lens 16, which are offset by ΔX' and ΔY' in the X'Y' coordinate system of pupil 10. $\Delta X' = X_p - X_c$ and $\Delta Y' = Y_p - Y_c$, wherein ($X_p$, $Y_p$) are the XY coordinates of pupil center 12 and ($X_c$, $Y_c$) are the coordinates of contact lens' center 14. L=the hypotenuse of right triangle ABC, which is calculated by Eq. (11). The interior angle, ϕ, of triangle ABC is given by Eq. (12). In this example, the rotation angle, α, equals zero (i.e., no rotation of contact lens 16).

Figure 17:
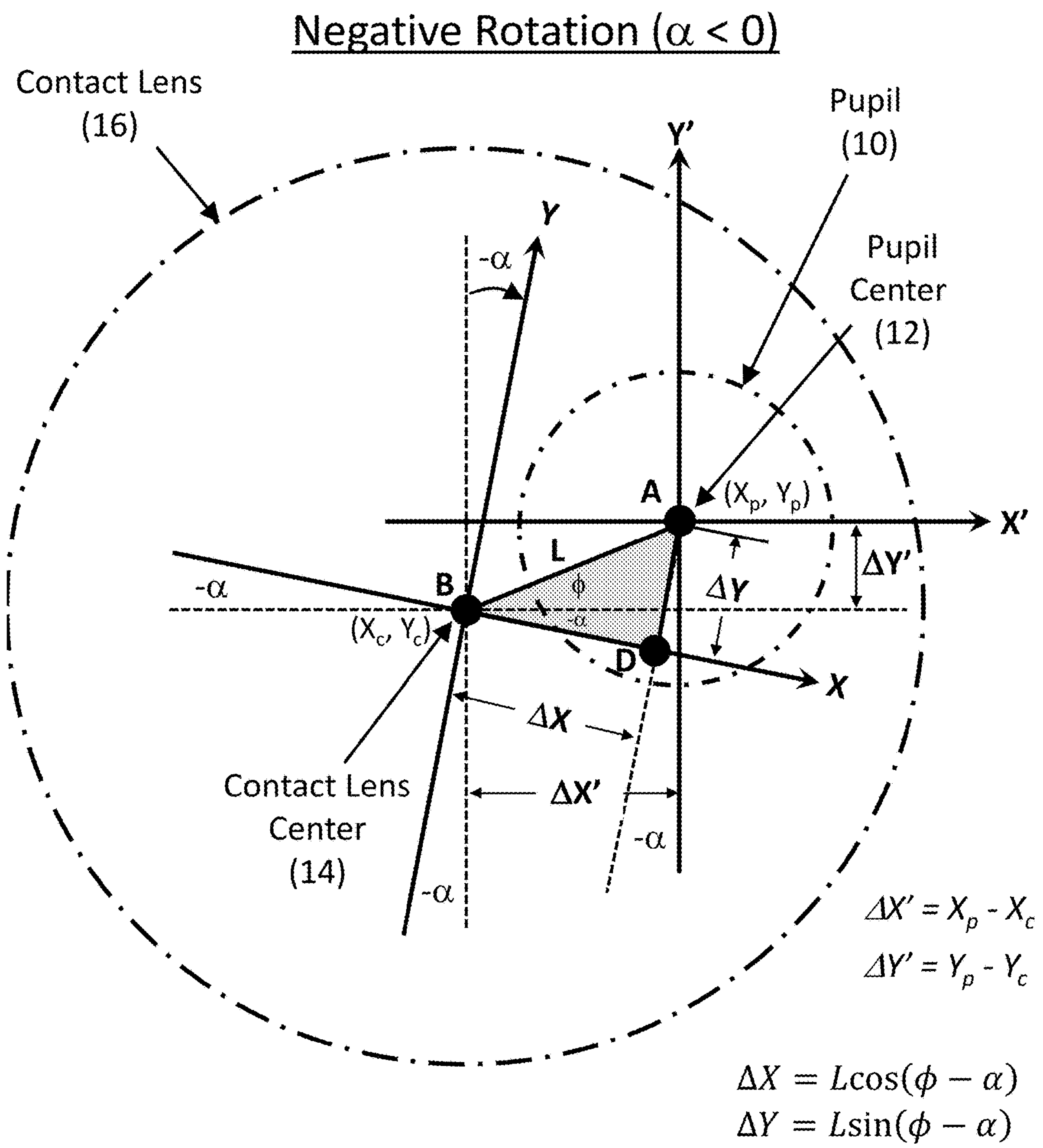
FIG. 17 shows a schematic example of a geometric layout of a pupil and a contact lens that is offset in the XY plane from the center of the pupil, with negative rotational angle, $-\alpha$, according to the present disclosure.

FIG. 17 shows a schematic example of a geometric layout of pupil 10 and contact lens 16 that is offset in the XY plane from pupil 10, with a negative rotational angle, −α, according to the present disclosure. Note that the amount of XY offset is exaggerated in this Figure to better illustrate the geometrical relationships among the different geometries. Two different coordinate systems are used: XY coordinates for contact lens 16, and X'Y' coordinates for pupil 10. This figure shows the geometric relationship between pupil center 12 of pupil 10 and contact lens center 14 of contact lens 16, which are offset by ΔX and ΔY in the rotated, local XY coordinate system of contact lens 16. ΔX=Lcos(ϕ−α) and ΔY=L sin(ϕ−α). ($X_p$, $Y_p$) are the XY coordinates of pupil center 12 and ($X_c$, $Y_c$) are the coordinates of contact lens' center 14. L=the hypotenuse of right triangle ABD and is calculated by $$L = \sqrt{(AC)^2 + (BC)^2}.$$

The interior angle, (ϕ−α) of right triangle ABD is shown. In this example, the rotation angle, α, is a negative number, which corresponds to a clockwise rotation of contact lens 16 with respect to a vertical axis. Note that ΔX=ΔX' and ΔY=ΔY' when the rotation angle, α, equals zero.

Figure 18:
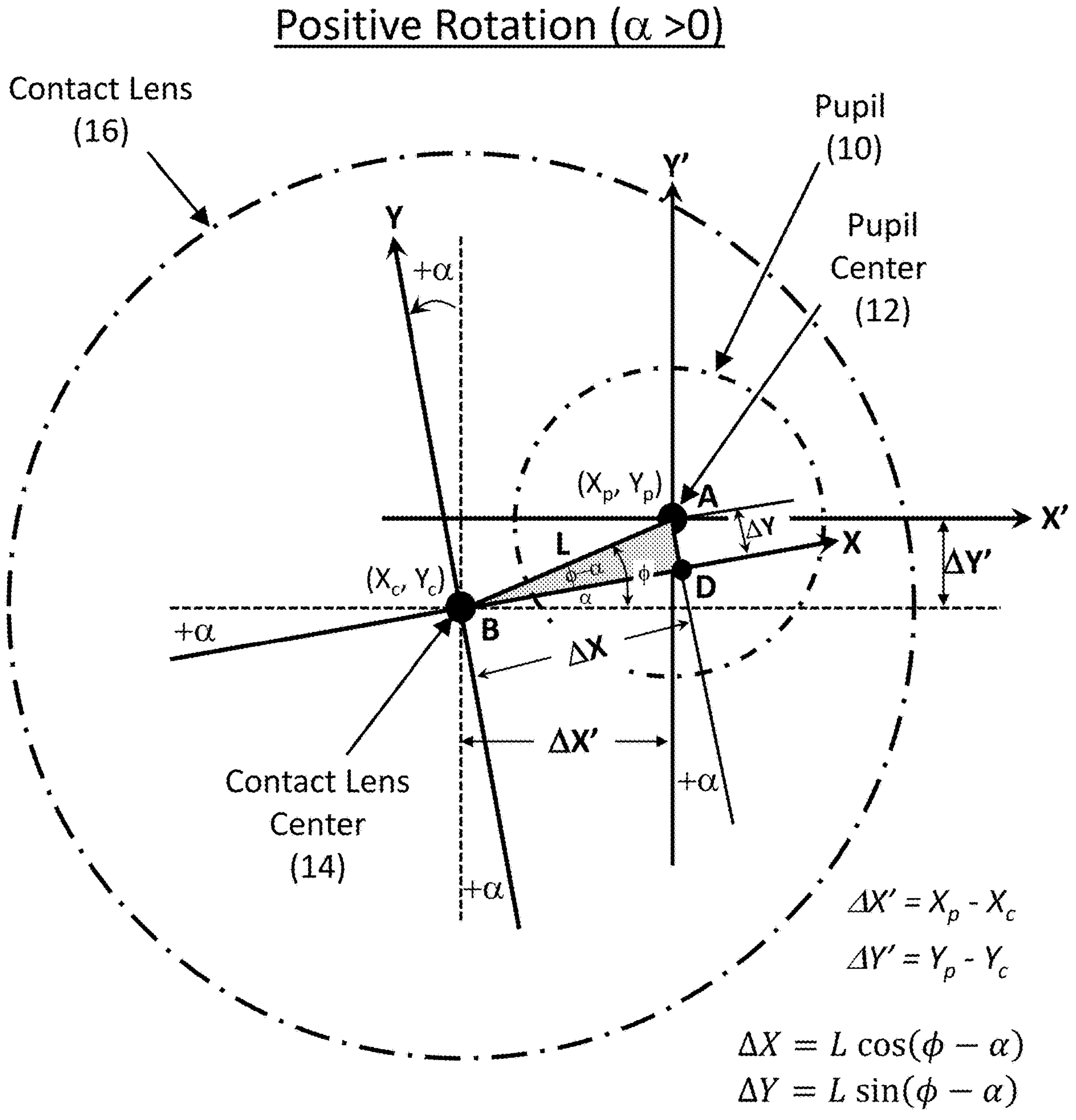
FIG. 18 shows a schematic example of a geometric layout of a pupil and a contact lens that is offset in the XY plane from the center of the pupil, with a positive rotational angle, $\alpha$, according to the present disclosure.

FIG. 18 shows a schematic example of a geometric layout of pupil 10 and contact lens 16 that is offset in the XY plane from pupil 10, with a positive rotational angle, α, according to the present disclosure. Note that the amount of XY offset is exaggerated in this Figure to better illustrate the geometrical relationships among the different geometries. Two different coordinate systems are used: XY coordinates for contact lens 16, and X'Y' coordinates for pupil 10. This figure shows the geometric relationship between pupil center 12 of pupil 10 and contact lens center 14 of contact lens 16, which are offset by ΔX and ΔY in the rotated, local XY coordinate system of contact lens 16. ΔX=Lcos(ϕ−α) and ΔY=L sin(ϕ−α). ($X_p$, $Y_p$) are the XY coordinates of pupil center 12 and ($X_c$, $Y_c$) are the coordinates of contact lens' center 14. L=the hypotenuse of right triangle ABD and is calculated by $$L = \sqrt{(AC)^2 + (BC)^2}.$$

The interior angle, (ϕ−α) of right triangle ABD is shown. In this example, the rotation angle, α, is a positive number, which corresponds to a counter-clockwise rotation of contact lens 16 with respect to a vertical axis. Note that ΔX=ΔX' and ΔY=ΔY' when the rotation angle, α, equals zero.

What is claimed is:

1. A method for determining an offset position and a rotation angle of a wavefront-customized correction patch for a wavefront-customized contact lens, the method comprising:

placing a Contact Lens (CL) on a patient's eye;

measuring an offset position and a rotation angle of the contact lens relative to a pupil of the patient's eye; and calculating a real center, ($X_c$, $Y_c$), of the contact lens by:

(1) providing a Radius of Curvature=R, Sagittal height=$S_0$, and Diameter=d of the contact lens;

(2) measuring, with an optical instrument, a pair of XY coordinates ($X_V$, $Y_V$) of a Corneal Vertex Normal by using a Corneal Topography (CT) and/or a visual Eye Imaging (EI) technique;

(3) determining a virtual center ($X_e$, $Y_e$) of the CL by fitting an edge of the contact lens to a circle or ellipse by using the diameter, d;

(4) calculating X- and Y-tilt angles ($\theta_x$d, $\theta_y$) by using equations (7) and (8), as follows:

$$\theta_x = \tan^{-1}\frac{X_v - X_e}{R} \quad \text{(Eq. 7)}$$

$$\theta_x = \tan^{-1}\frac{X_v - X_e}{R}. \quad \text{(Eq. 8)}$$

and (5) calculating the real center ($X_c$, $Y_c$) of the contact lens by using equations (9) and (10), as follows:

$$X_c = X_e + S_0\sin\theta_x \text{ and} \quad \text{(Eq. 9)}$$

$$Y_c = Y_e + S_0\sin\theta_y; \quad \text{(Eq. 10)}$$

wherein the contact lens does not have any fiducial marks.

2. The method of claim 1 further comprising using an optical instrument to measure the offset position and the rotation angle of the contact lens; wherein the optical instrument is chosen from an aberrometer, a corneal topographer (CT), an Optical Coherence Tomography (OCT) instrument, or a Scheimflug instrument, or combinations thereof.

3. The method of claim 1, wherein the contact lens is a contact lens that is used regularly by the patient.

4. The method of claim 1, further comprising determining a corneal vertex location by measuring and calibrating one or more front surface Purkinje reflections from the patient's eye.

5. The method of claim 1, wherein both the contact lens and the wavefront-customized contact lens are scleral contact lenses.

6. The method of claim 1, further comprising measuring the pair of Corneal Vertex coordinates ($X_V$, $Y_V$) by using one or more Purkinje reflections from the patient's eye.

7. The method of claim 6, further comprising calculating a pair of CL offsets (ΔX, ΔY) by using equations (11, 12, 13, and 14), as follows:

$$L = \sqrt{(X_P - X_c)^2 + (Y_P - Y_c)^2} \quad \text{(Eq. 11)}$$

$$\phi = \tan^{-1}\left(\frac{Y_P - Y_c}{X_P - X_c}\right) \quad \text{(Eq. 12)}$$

$$\Delta X = L\cos(\phi - \alpha) \quad \text{(Eq. 13)}$$

$$\text{and } \Delta Y = L\sin(\phi - \alpha); \quad \text{(Eq. 14)}$$

wherein $X_p$ and $Y_p$ are XY coordinates, respectively, of a center of the patient's pupil.

8. The method of claim 1, further comprising measuring one or more tilt angles of the contact lens by determining an optical Z-axis normal of the optical instrument.

9. The method of claim 8, further comprising projecting light through an objective front lens of the optical instrument and finding a position of the optical Z-axis normal.

10. The method of claim 1, wherein the optical instrument comprises a corneal topographer combined with a wavefront aberrometer.

11. The method of claim 1, further comprising:

(a) placing the contact lens on the patient's eye;

(b) measuring, with the optical instrument, a pair of XY offsets (ΔX, ΔY) of a center of the contact lens while sitting on the patient's eye;

(c) measuring a rotation angle, «, around the Z-axis, of the contact lens while sitting on the patient's eye;

(d) determining an optimal XY location and an optimal angular orientation of a wavefront-guided correction patch on a wavefront-customized contact lens by using the pair of XY offsets (ΔX, ΔY) and the rotation angle, α, of the contact lens;

(e) defining a center of the wavefront-guided correction patch; and (f) adjusting a placement of the wavefront-guided correction patch on a wavefront-customized contact lens by:

(1) placing the center of the wavefront-guided correction patch at the optimal XY location by X- and Y-distances equal to the pair of offsets (ΔX, ΔY), respectively, and by (2) rotating the wavefront-guided correction patch by the rotation angle, α, to the optimal angular orientation.

12. The method of claim 11, wherein the optical instrument comprises a combined corneal topographer and a wavefront aberrometer.

13. The method of claim 1, further comprising minimizing aberrations of the patient's eye by fabricating and using an optimized wavefront-customized contact lens, the method comprising:

(a) measuring one or more aberrations of a patient's eye with the optical instrument;

(b) designing a wavefront-guided correction patch for the optimized wavefront-customized contact lens by using the one or more measured aberrations of the patient's eye;

(c) placing a contact lens on the patient's eye;

(d) measuring a pair of XY offsets (ΔX, ΔY) of a center ($X_c$, $Y_c$) of the contact lens while sitting on the patient's eye;

(e) measuring a rotation angle, α, around the Z-axis, of the contact lens while sitting on the patient's eye;

(f) defining a center of the wavefront-guided correction patch;

(g) adjusting a placement of the wavefront-guided correction patch on the optimized wavefront-customized contact lens by:

(1) placing the center of the wavefront-guided correction patch at the pupil center by using the pair of ΔX and ΔY offsets, and by (2) rotating the wavefront-guided correction patch by the rotation angle, α;

(h) fabricating the optimized wavefront-customized contact lens with the adjusted placement of the wavefront-guided correction patch; and (i) minimizing the one or more aberrations of the patient's eye by using the optimized wavefront-customized contact lens on the patient's eye.

14. The method of claim 13, wherein the optical instrument comprises a combined corneal topographer and a wavefront aberrometer.

* * * * *